(12) United States Patent
Takebe et al.

(10) Patent No.: US 10,713,539 B2
(45) Date of Patent: Jul. 14, 2020

(54) RECORDING MEDIUM, CASE DATA GENERATION SUPPORT SYSTEM, AND CASE DATA GENERATION SUPPORT METHOD

(71) Applicant: FUJITSU LIMITED, Kawasaki-shi, Kanagawa (JP)

(72) Inventors: Hiroaki Takebe, Kawasaki (JP); Masaki Ishihara, Kawasaki (JP); Masahiko Sugimura, Kawasaki (JP); Susumu Endo, Kawasaki (JP); Takayuki Baba, Kawasaki (JP); Yusuke Uehara, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 184 days.

(21) Appl. No.: 15/987,023

(22) Filed: May 23, 2018

(65) Prior Publication Data
US 2018/0268263 A1  Sep. 20, 2018

Related U.S. Application Data

(63) Continuation of application No. PCT/JP2015/083328, filed on Nov. 27, 2015.

(51) Int. Cl.
| | | |
|---|---|---|
| *G06K 9/62* | (2006.01) | |
| *G16H 50/20* | (2018.01) | |
| *A61B 6/00* | (2006.01) | |
| *G06T 11/20* | (2006.01) | |
| *G16H 10/60* | (2018.01) | |
| *G16H 40/63* | (2018.01) | |

(Continued)

(52) U.S. Cl.
CPC .......... *G06K 9/6269* (2013.01); *A61B 6/5217* (2013.01); *G06K 9/628* (2013.01);
(Continued)

(58) Field of Classification Search
CPC .. G06K 9/6269; G06K 9/6254; G06K 9/6263; G06K 9/628; G06K 9/6285;
(Continued)

(56) References Cited

U.S. PATENT DOCUMENTS

2005/0169517 A1    8/2005  Kasai
2008/0240494 A1   10/2008  Oosawa et al.
(Continued)

FOREIGN PATENT DOCUMENTS

JP    2001-250101    9/2001
JP    2005-198970    7/2005
(Continued)

OTHER PUBLICATIONS

International Search Report for International Patent Application No. PCT/JP2015/083328, dated Jan. 19, 2016.
(Continued)

*Primary Examiner* — Leon Flores
(74) *Attorney, Agent, or Firm* — Staas & Halsey LLP

(57) ABSTRACT

A non-transitory recording medium stores a program causing a computer to execute a process including determining a reference value on a decision surface classifying a group of image data represented by a plurality of types of feature quantities into two classes in a feature quantity space, based on a feature quantity of given image data that is closest to the decision surface and is classified into one of the classes of the group of image data in the feature quantity space, plotting and displaying pieces of image data of the group of image data along at least one axis indicating a degree of separation of each of the pieces of image data relative to the reference value, modifying, upon receiving a single piece of image data identified from the plotted and displayed pieces of image data, the decision surface based on the identified single piece of image data.

7 Claims, 19 Drawing Sheets

(51) Int. Cl.
*G16H 30/20* (2018.01)
*G06T 7/00* (2017.01)
*A61B 6/03* (2006.01)

(52) U.S. Cl.
CPC ......... *G06K 9/6254* (2013.01); *G06K 9/6263* (2013.01); *G06K 9/6285* (2013.01); *G06T 7/0012* (2013.01); *G06T 11/206* (2013.01); *G16H 10/60* (2018.01); *G16H 30/20* (2018.01); *G16H 40/63* (2018.01); *G16H 50/20* (2018.01); *A61B 6/032* (2013.01); *A61B 6/463* (2013.01); *G06T 2200/24* (2013.01); *G06T 2207/20072* (2013.01); *G06T 2207/30096* (2013.01)

(58) Field of Classification Search
CPC ........ G16H 30/20; G16H 50/20; G16H 40/63; A61B 6/5217; G06T 7/0012; G06T 11/206
See application file for complete search history.

(56) References Cited

U.S. PATENT DOCUMENTS

| | | |
|---|---|---|
| 2008/0247619 A1 | 10/2008 | Li |
| 2010/0063948 A1* | 3/2010 | Virkar ................... G06N 20/00 706/12 |
| 2013/0243244 A1 | 9/2013 | Miyamoto et al. |

FOREIGN PATENT DOCUMENTS

| | | |
|---|---|---|
| JP | 2005-352997 | 12/2005 |
| JP | 2008-245719 | 10/2008 |
| JP | 2008-253292 | 10/2008 |
| JP | 2009-070284 | 4/2009 |
| JP | 2013-192624 | 9/2013 |

OTHER PUBLICATIONS

Espacenet English Abstract for JP 2013-192624, published Sep. 30, 2013.
Espacenet English Abstract for JP 2008-253292, published Oct. 23, 2008.
Espacenet English Abstract for JP 2008-245719, published Oct. 16, 2008.
Espacenet English Abstract for JP 2001-250101, published Sep. 14, 2001.
Espacenet English Abstract for JP 2005-325997, published Dec. 22, 2005.
Espacenet English Abstract for JP 2009-070284, published Apr. 2, 2009.
Espacenet English Abstract for JP 2005-198970, published Jul. 28, 2005.

* cited by examiner

FIG.3

| 114-1 | | | |
|---|---|---|---|
| PATIENT NAME | AGE | GENDER | CURRENT MEDICAL HISTORY |
| DATE AND TIME OF CT SCAN | 6/10/2015 | 8/23/2015 | 11/1/2015 |
| SCANNED BODY PART | LUNG | LUNG | LUNG |
| SERIES NAME | SERIES A | SERIES B | SERIES C |
| CT IMAGE DATA GROUP | ImageA001<br>ImageA002<br>ImageA003<br>．<br>．<br>．<br>ImageA015<br>ImageA016<br>ImageA017<br>ImageA018<br>．<br>．<br>．<br>ImageA030 | ImageB001<br>ImageB002<br>ImageB003<br>．<br>．<br>．<br>ImageB015<br>ImageB016<br>ImageB017<br>ImageB018<br>．<br>．<br>．<br>ImageB030 | ImageC001<br>ImageC002<br>ImageC003<br>．<br>．<br>．<br>ImageC015<br>ImageC016<br>ImageC017<br>ImageC018<br>．<br>．<br>．<br>ImageC030 |
| EXTRACTED REGION DATA | RegionA01 | RegionB01 | RegionC01 |

301, 302, 303

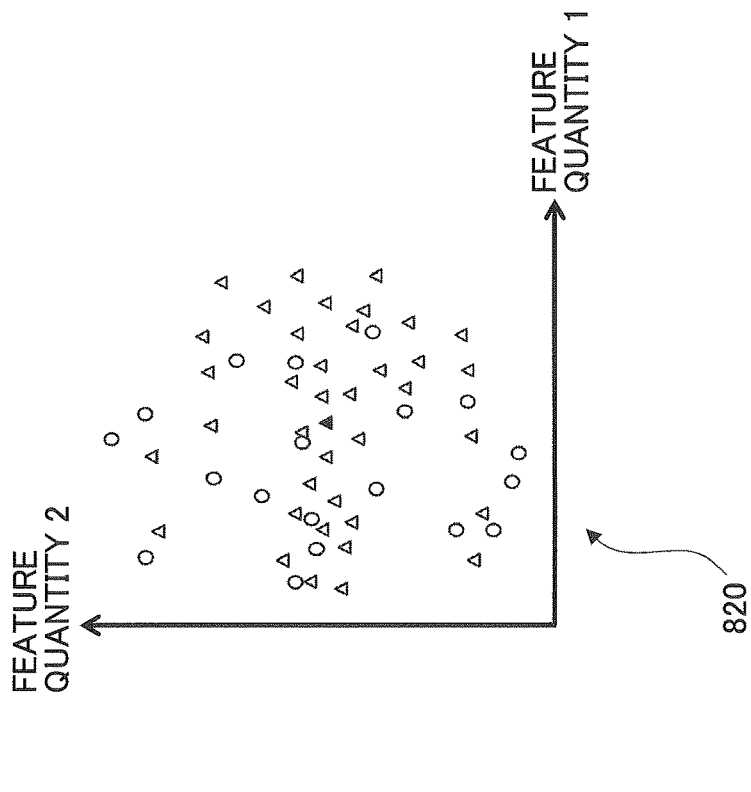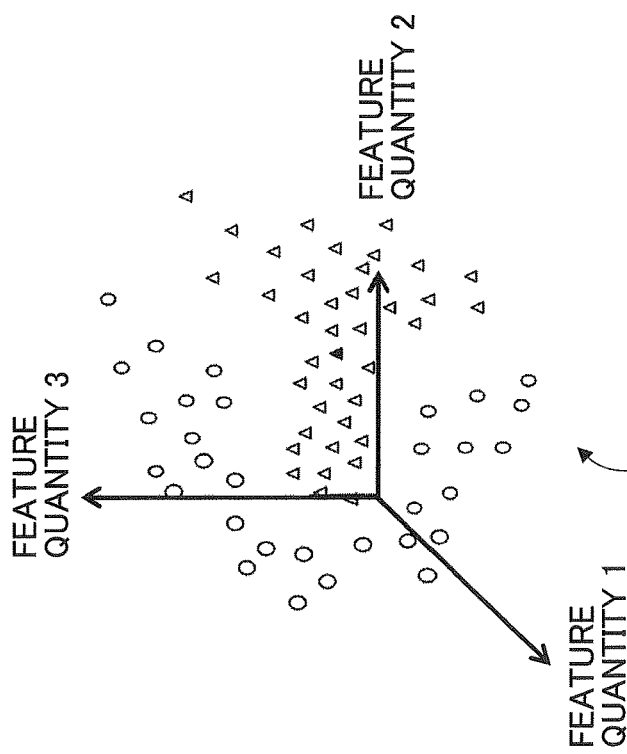

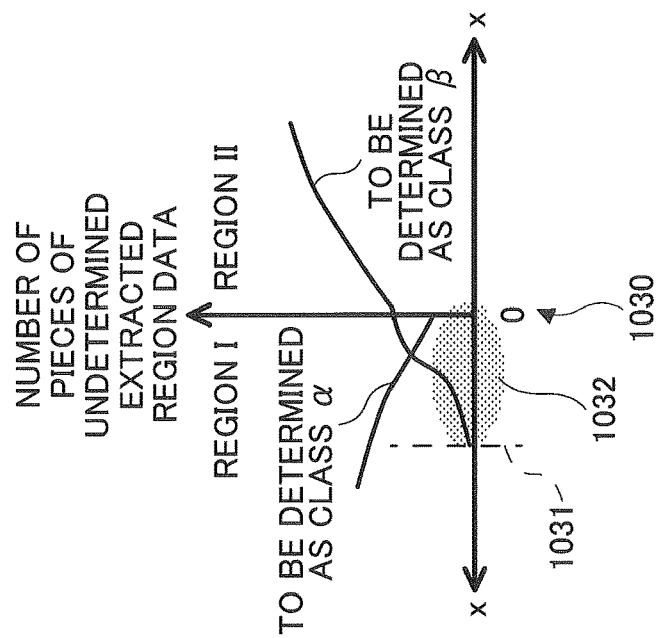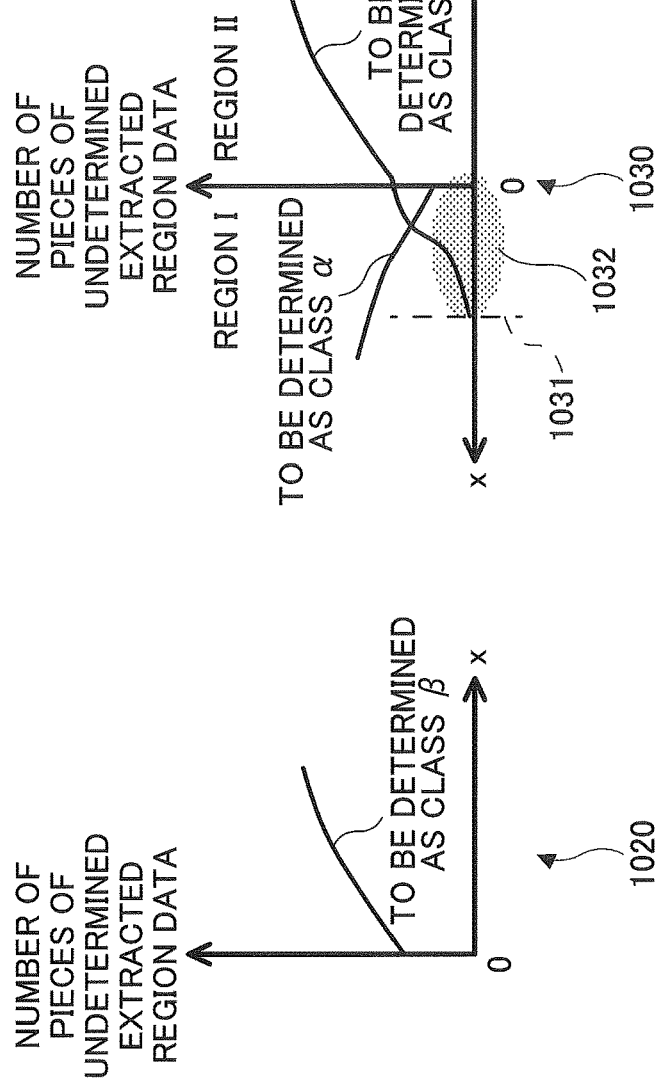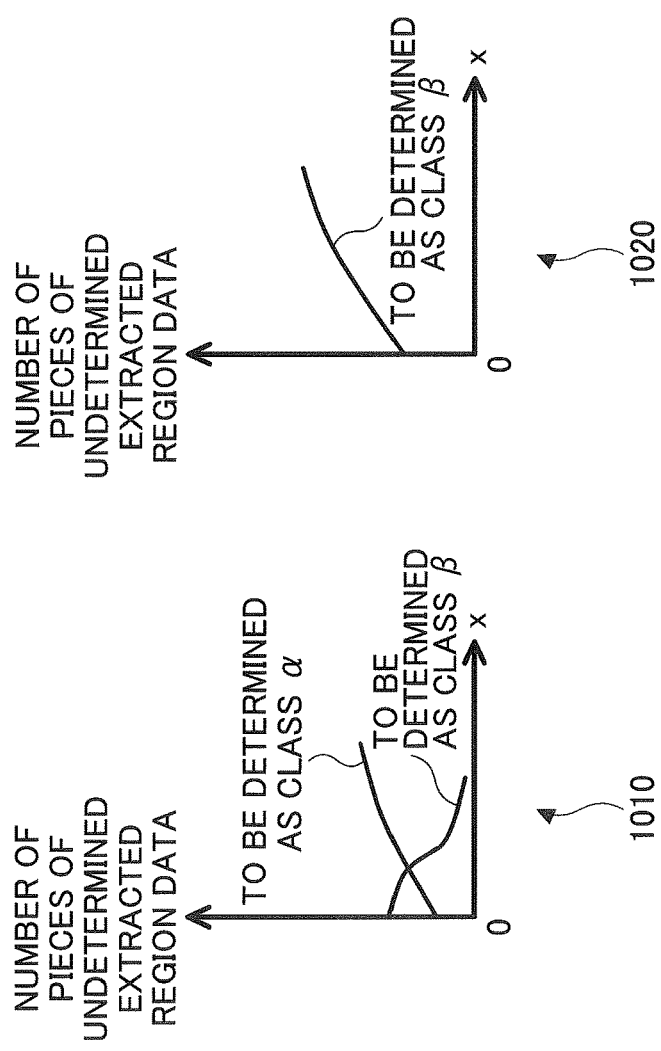

RECORDING MEDIUM, CASE DATA GENERATION SUPPORT SYSTEM, AND CASE DATA GENERATION SUPPORT METHOD

CROSS-REFERENCE TO RELATED APPLICATIONS

This application is a continuation application of International Application PCT/JP2015/083328 filed on Nov. 27, 2015 and designated the U.S., the entire contents of which are incorporated herein by reference.

FIELD

The disclosures herein generally relate to a recording medium, a case data generation support system, and a case data generation support method.

BACKGROUND

Conventionally, diagnosis of diseases (for example, a tumor region) has been performed by using CT (computed tomography) scanned image data in medical sites. In order to reduce the burden on a doctor when diagnosis is performed, a diagnosis support system is used. With the diagnosis support system, disease case data similar to a diagnosis target can be retrieved from a database storing previous case data and the retrieved similar case data can be displayed.

In order to create a database storing case data, it is required to extract, as case data, image data of a given region from previously taken CT image data, and determine whether the extracted case data includes tumor regions. At this time, when the number of pieces of case data is very large, the case data needs to be machine determined. Further, in order to machine determine the case data, boundary surfaces need to be calculated. The boundary surfaces are used to classify case data known to include tumor regions and case data known to not include tumor regions into respective classes.

However, as some tumor regions are similar to tissues inside the human body, it is not easy to calculate boundary surfaces suitable to determining whether case data includes tumor regions. Therefore, for boundary surfaces used to determine case data, undetermined case data that does not belong to either class is generated. In this case, a doctor determines to which class the undetermined case data belongs, and the boundary surfaces are also modified based on the class determined by the doctor. As a result, accuracy of determining whether data includes tumor regions can be enhanced.

When the boundary surfaces are modified based on the result determined by the doctor, it is desirable for the doctor to select, from the above-described undetermined case data, case data having a highly enhanced effect in terms of determination accuracy in modifying the boundary surfaces. By selecting such case data, the number of times the boundary surfaces are modified can be reduced, and thus, the modification work load can be reduced.

However, such boundary surfaces are defined in a high-dimensional feature space according to feature quantities of each case data. It is thus difficult to recognize case data having a highly enhanced effect in terms of determination accuracy.

RELATED-ART DOCUMENTS

Patent Document

[Patent Document 1] Japanese Laid-open Patent Publication No. 2005-352997

SUMMARY

According to an aspect of at least one embodiment, a non-transitory recording medium stores a program causing a computer to execute a case data generation support process including determining a reference value on a decision surface classifying a group of image data represented by a plurality of types of feature quantities into two classes in a feature quantity space, based on a feature quantity of given image data that is closest to the decision surface and is classified into one of the classes of the group of image data in the feature quantity space, plotting and displaying pieces of image data of the group of image data along at least one axis indicating a degree of separation of each of the pieces of image data relative to the reference value, modifying, upon receiving a single piece of image data identified from the plotted and displayed pieces of image data, the decision surface based on the identified single piece of image data.

The object and advantages of the embodiment will be realized and attained by means of the elements and combinations particularly pointed out in the claims. It is to be understood that both the foregoing general description and the following detailed description are exemplary and explanatory and are not restrictive of the invention, as claimed.

BRIEF DESCRIPTION OF DRAWINGS

FIG. 3 is a drawing illustrating a configuration of a CT image data storage DB;

FIGS. 8A and 8B are graphs for explaining a problem with a method of presenting undetermined extracted region data;

FIGS. 10A through 10O are graphs for explaining a relationship between an index x and undetermined extracted region data;

DESCRIPTION OF EMBODIMENTS

Figure 1:
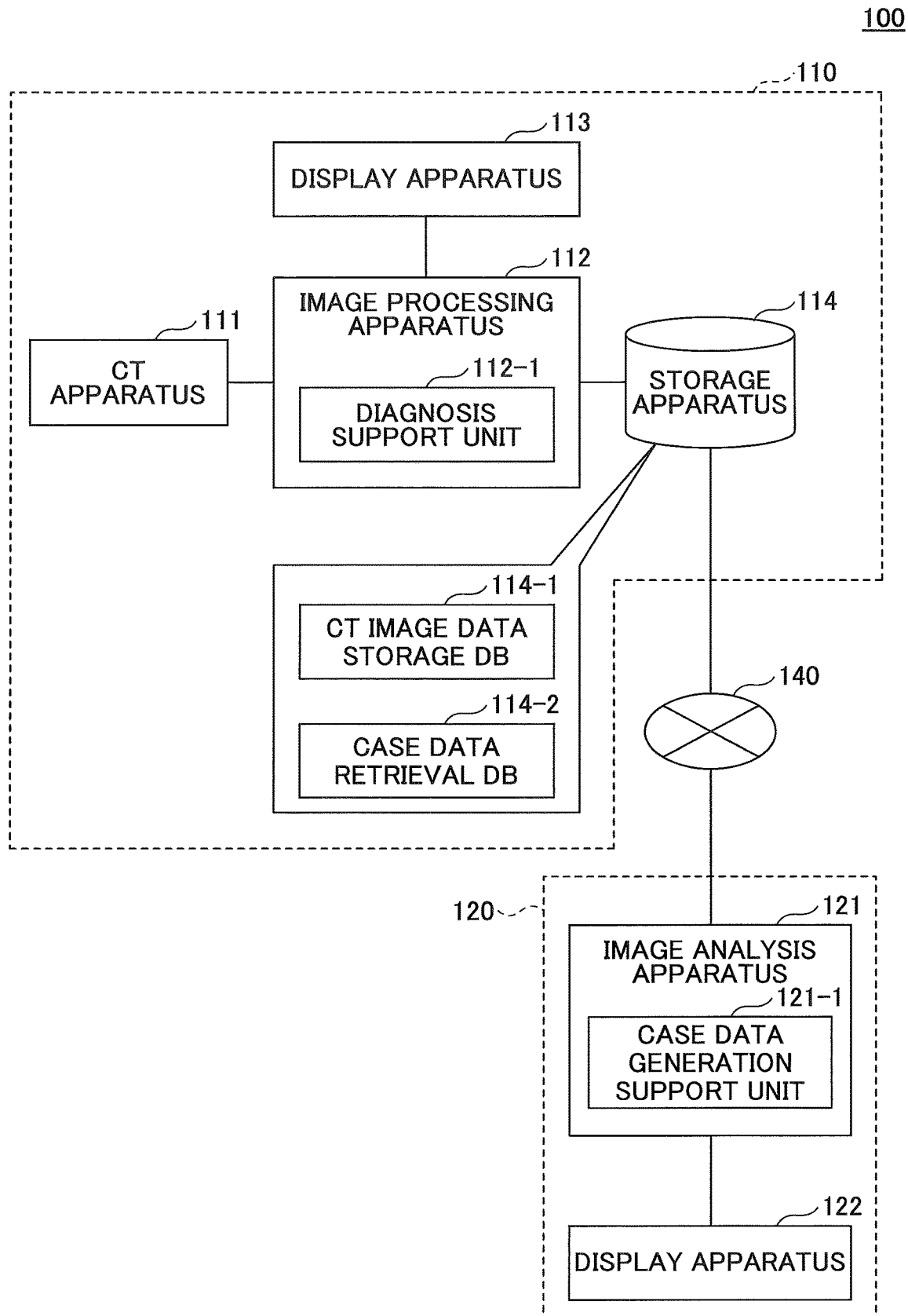
FIG. 1 is a drawing illustrating an example of a diagnosis support system.

In the following, embodiments of the present invention will be described with reference to the accompanying drawings.

A case data generation support system described in the following embodiments supports a doctor or other health professional in modifying "boundary surfaces" used to classify a group of image data into classes.

"Boundary surfaces" are virtual planes indicating boundaries of respective classes. The boundary surfaces are calculated by inputting image data with known classes into a learning model and classifying the group of image data into the classes. Accordingly, the boundary surfaces change according to the image data with known classes, which has been input into the learning model.

The boundary surfaces are defined for respective classes. In the following embodiments, a boundary surface of one class to which data including tumor regions belongs and a boundary surface of another class to which all other data belongs are defined. However, classes defined by the boundary surfaces are not limited thereto.

Further, the boundary surfaces are used to determine unknown classes of image data. In a case where image data whose class is unknown is located inside the boundary surface of the one class to which data including tumor regions belongs, the image data is determined as data including tumor regions. Conversely, in a case where image data whose class is unknown is located inside the boundary surface of the other class to which other data belongs, the image data is determined as other data.

Further, in the following embodiments, "image data with known classes" and "image data with unknown classes" are included in image data before a class determination process based on the boundary surfaces are performed. The "image data with known classes" is inputted into the learning model, classified into a corresponding class, and used to calculate boundary surfaces. The "image data with unknown classes" are used to perform the class determination process based on the boundary surfaces calculated by using the "image data with known classes".

Moreover, "image data with determined classes" and "image data with undetermined classes" are included in the image data after the class determination process is performed based on the boundary surfaces. The "image data with determined classes" refers to image data determined as being located inside the boundary surface of each of the classes (determined as image data including tumor regions or other image data). The "image data with undetermined classes" refers to image data determined as being located outside the boundary surface of each of the classes.

In the following embodiments, a "decision surface" refers to a virtual intermediate plane between boundary surfaces of each class. The decision surface is used as reference surface to select image data whose class is to be determined by a doctor or other health professional.

In the following, the embodiments of the present invention will be described in detail with reference to the accompanying drawings. In the specification and the drawings, elements having substantially the same functions or configurations are denoted by the same reference numeral, and a duplicate description thereof will be omitted.

First Embodiment

First, a diagnosis support system including a CT (computed tomography) imaging system configured to take CT images and a case data generation support system according to a first embodiment will be described. FIG. 1 is a drawing illustrating an example of the diagnosis support system.

As illustrated in FIG. 1, a diagnosis support system 100 includes a CT imaging system 110 and a case data generation support system 120.

The CT imaging system 110 includes a CT apparatus 111, an image processing apparatus 112, a display apparatus 113, and a storage apparatus 114. The CT apparatus 111 and the image processing apparatus 112 are electrically coupled to each other and various types of data are transmitted and received between the two apparatuses. Also, the image processing apparatus 112 and the storage apparatus 114 are electrically coupled to each other and various types of data are transmitted and received between the two apparatuses.

The CT apparatus 111 scans the inside of the body of a patient by using radiation and performs processing by using a computer such that CT images that are cross-sectional images or slices of the scanned patient are produced (this process is hereinafter referred to as "to take CT images"). The CT apparatus 111 transmits the CT scanned images to the image processing apparatus 112.

The image processing apparatus 112 stores the CT images taken by the CT apparatus in a CT image data storage database (DB) of the coupled storage apparatus 114. Further, a diagnosis support program is installed in the image processing apparatus 112. The image processing apparatus 112 functions as a diagnosis support unit 112-1 by causing the diagnosis support program to be executed by the computer.

The diagnosis support unit 112-1 reads CT image data taken at different times and stored in the CT image data storage DB 114-1, and displays the CT image data on the display apparatus 113. Thereby, a doctor can perform comparative reading for comparing the CT images of a tumor region of a patient taken at different times.

Further, when a given region is designated in CT image data currently used for diagnosis, the diagnosis support unit 112-1 retrieves similar case data including tumor regions and displays the case data on the display apparatus 113. Namely, it is possible for the doctor to retrieve similar cases based on the given region designated in the CT image data currently used for diagnosis.

The storage apparatus 114 receives the CT image data taken by the CT apparatus 111 via the image processing apparatus 112, and stores the CT image data in the CT image data storage DB 114-1. Also, the storage apparatus 114 extracts image data of the given region extracted from the CT image data (hereinafter referred to as "extracted region data") into the CT image data storage DB 114-1. The extracted region data includes image data including tumor regions and image data not including tumor regions, both of which are represented by a plurality of types of feature quantities.

Further, the storage apparatus 114 stores case data (extracted region data used to retrieve similar cases) generated by the case data generation support system 120 into the case data retrieval DB 114-2.

The case data generation support system 120 includes an image analysis apparatus 121 and a display apparatus 122. The image analysis apparatus 121 and the storage apparatus 114 are communicably coupled to each other via a network 140. The image analysis apparatus 121 can access the storage apparatus 114 via the network 140.

A case data generation support program is installed in the image analysis apparatus 121. The image analysis apparatus 121 functions as a case data generation support unit 121-1 by causing the data generation support program to be executed by the computer.

The case data generation support unit 121-1 includes a learning model (for example, a support vector machine (SVM)) for calculating "boundary surfaces" used to machine determine whether extracted region data of unknown class includes tumor regions (namely, the boundary surfaces used to perform the class determination process). Also, the case data generation support unit 121-1 reads extracted region data that is stored in the CT image data storage DB 114-1 and is unknown as to whether tumor regions are included, and calculates "boundary surfaces" used to determine whether tumor regions are included.

Further, for extracted region data that is unknown as to whether tumor regions are included, the case data generation support unit 121-1 performs the class determination process for machine determining whether tumor regions are included based on the boundary surfaces. Also, for extracted region data determined as not belonging to either the tumor region class or the other class (undetermined extracted region data) as a result of the class determination process, the doctor determines whether the extracted region data includes tumor regions. The case data generation support unit 121-1 receives a determination result by the doctor. Based on the received determination result, the case data generation support unit 121-1 modifies the boundary surfaces and updates the case data retrieval DB 114-2.

Figure 2:
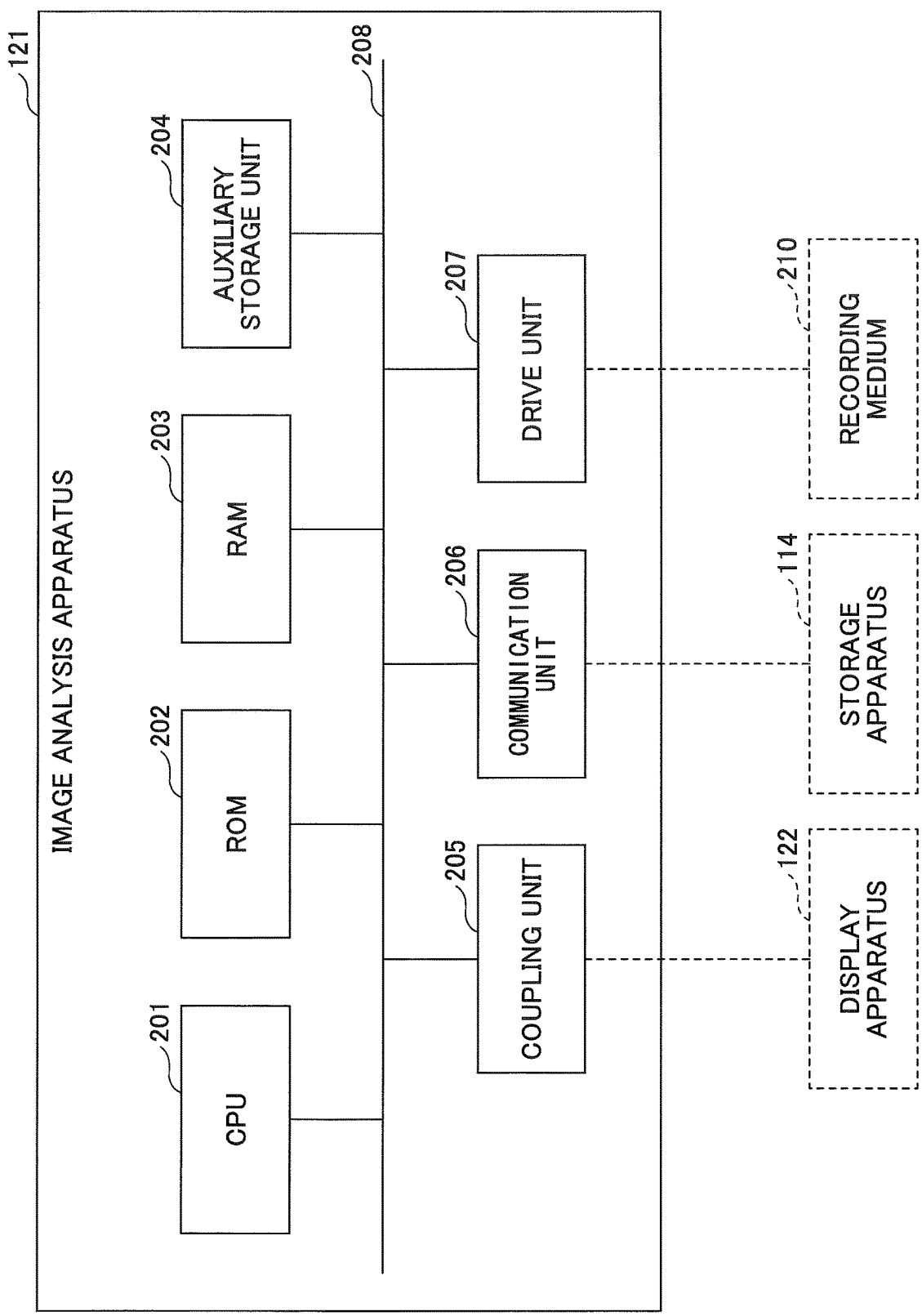
FIG. 2 is a drawing illustrating a hardware configuration of an image analysis apparatus.

Next, a hardware configuration of the image analysis apparatus 121 will be described. FIG. 2 is a drawing illustrating the hardware configuration of the image analysis apparatus. As illustrated in FIG. 2, the image analysis apparatus 121 includes central processing unit (CPU) 201, read-only memory (ROM) 202, random-access memory (RAM) 203, and an auxiliary storage unit 204. Further, the image analysis apparatus 121 includes a coupling unit 205, a communication unit 206, and a drive unit 207. Further, the units of the image analysis apparatus 121 are coupled to each other via a bus 208.

The CPU 201 is a computer that executes various programs (for example, the case data generation support program) stored in the auxiliary storage unit 204.

The ROM 202 is non-volatile memory. The ROM 202 functions as a main storage unit that stores various programs and data used for the CPU 201 to execute the various programs stored in the auxiliary storage unit 204. Specifically, the ROM 202 stores boot programs such as Basic Input/Output System (BIOS) and Extensible Firmware Interface (EFI).

The RAM 203 is volatile memory, and includes dynamic random-access memory (DRAM) and static random-access memory (SRAM). The RAM 203 is a main storage unit that provides a working area in which the various programs stored in the auxiliary storage unit 204 are deployed when executed by the CPU 201.

The auxiliary storage unit 204 is a computer-readable storage apparatus in which the various programs installed in the image analysis apparatus 121 and data generated by execution of the various programs are recorded.

The coupling unit 205 is coupled to the display apparatus 122. Various types of data are transmitted and received between the coupling unit 205 and the display apparatus 122. The image analysis apparatus 121 causes the display apparatus 122 to display various types of screens and receives various instructions input through the display apparatus 122.

The communication unit 206 communicates with the storage apparatus 114 via the network 140. The drive unit 207 is a device for setting a recording medium 210. As used herein, the recording medium 210 includes media that optically, electrically, or magnetically records information, such as a CD-ROM, a flexible disk, or a magneto-optical disc. Further, the recording medium 210 includes semiconductor memory that electrically records information, such as ROM and flash memory.

Further, the various programs stored in the auxiliary storage unit 204 are installed by inserting, for example, the distributed recording medium 210 into the drive unit 207 and reading the various programs recorded in the recording medium 210 by the drive unit 207. Alternatively, the various programs stored in the auxiliary storage unit 204 may be installed by downloading the various programs from the network 140 via the communication unit 206.

Next, a configuration of the CT image data storage DB 114-1 will be described. FIG. 3 is a drawing illustrating the configuration of the CT image data storage DB. As illustrated in FIG. 3, in the CT image data storage DB 114-1, CT image data is managed and classified by patient. Specifically, the CT image data storage DB 114-1 stores information 301, 302, 303, and so on that includes CT image data classified by patient.

The information 301, 302, 303, and so on classified by patient has the same format. As an example herein, the information 301 classified by patient will be described. The information 301 classified by patient includes, as information items, "patient name," "age," "gender," and "current medical history" and the information items each store patient attribute information. Further, the information 301 classified by patient includes, as information items, "date and time of CT scan," "scanned body part," "series name," "CT image data group," and "extracted region data".

The "date and time of CT scan" and the "scanned body part" have CT scan-related attribute information. The "series name" includes a series name for identifying a series of CT image data taken by scanning a plurality of positions in the vertical direction of the patient.

The "CT image data group" stores a plurality of CT scanned image data files. The "extracted region data" includes region data extracted from CT image data.

Figure 4:
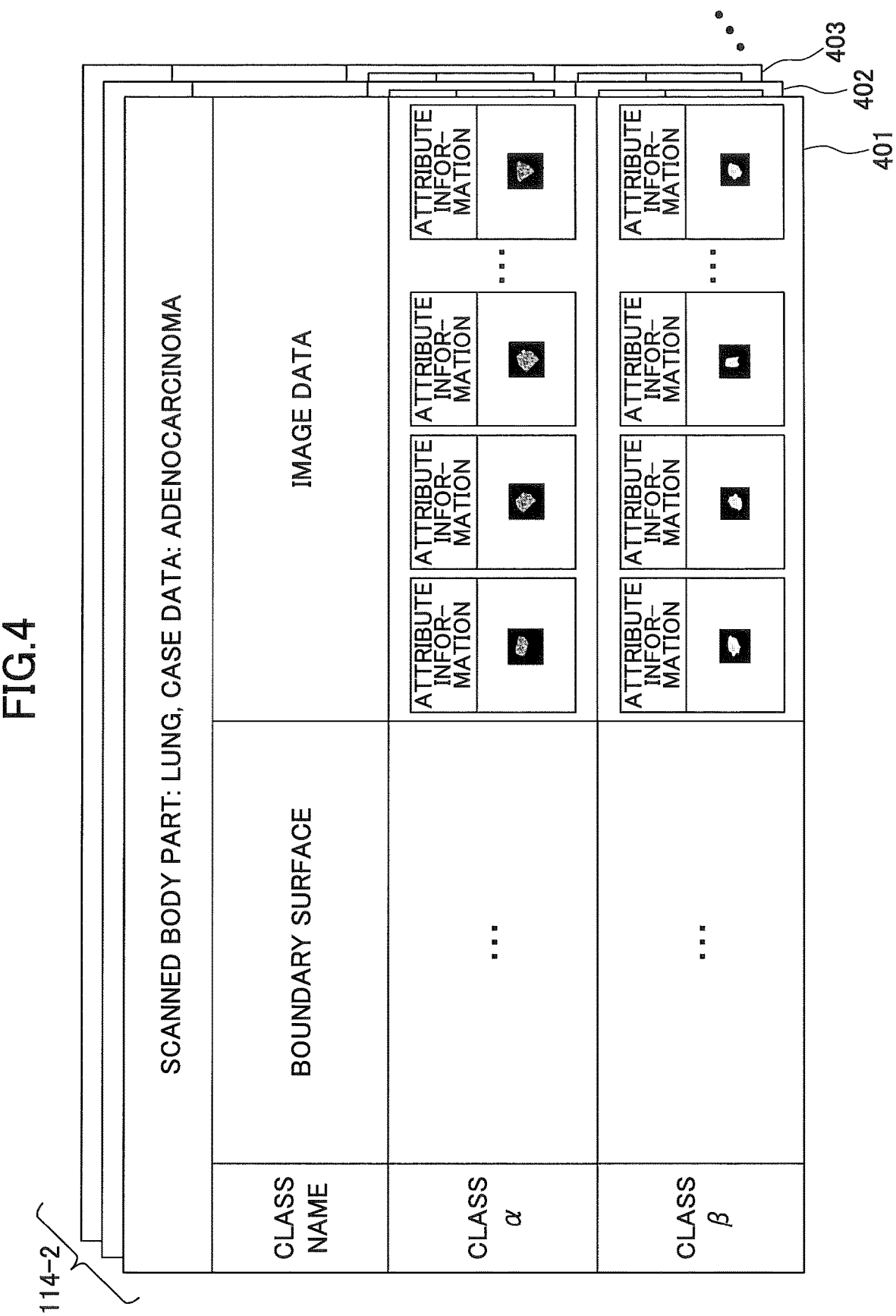
FIG. 4 is a drawing illustrating a configuration of a case data retrieval DB.

Next, a configuration of the case data retrieval DB 114-2 will be described. FIG. 4 is a drawing illustrating the configuration of the case data retrieval DB. As illustrated in FIG. 4, in the case data retrieval DB 114-2, case data is managed and classified by scanned body part and by case data. Specifically, the case data retrieval DB 114-2 stores information 401, 402, 403, and so on that includes case data classified by scanned body part and by case data.

The information 401, 402, 403, and so on classified by case data has the same format. As an example herein, the information 401 classified by case data will be described. The information 401 includes, as information items, "class name," "boundary surface," and "image data".

The "class name" stores a class name of each class. For example, the class name "class α" refers to a class name of a class to which data including tumor regions belongs, among region data extracted from CT image data. Also, the class name "class β" refers to a class name of a class to which data not including tumor regions belongs, among the region data extracted from the CT image data.

The "boundary surface" stores parameters for defining boundary surfaces indicating a boundary of each class (for example, a boundary of the class α and a boundary of the class β). For example, boundary surfaces are calculated by inputting image data with known classes into the SVM and grouping the input image data into classes. Such boundary surfaces are defined by support vectors and their coefficients.

The "image data" stores extracted region data whose classes are determined by the case data generation support unit 121-1. Each of the extracted region data stored in the "image data" is associated with patient attribute information and CT scan-related attribute information.

Figure 5:
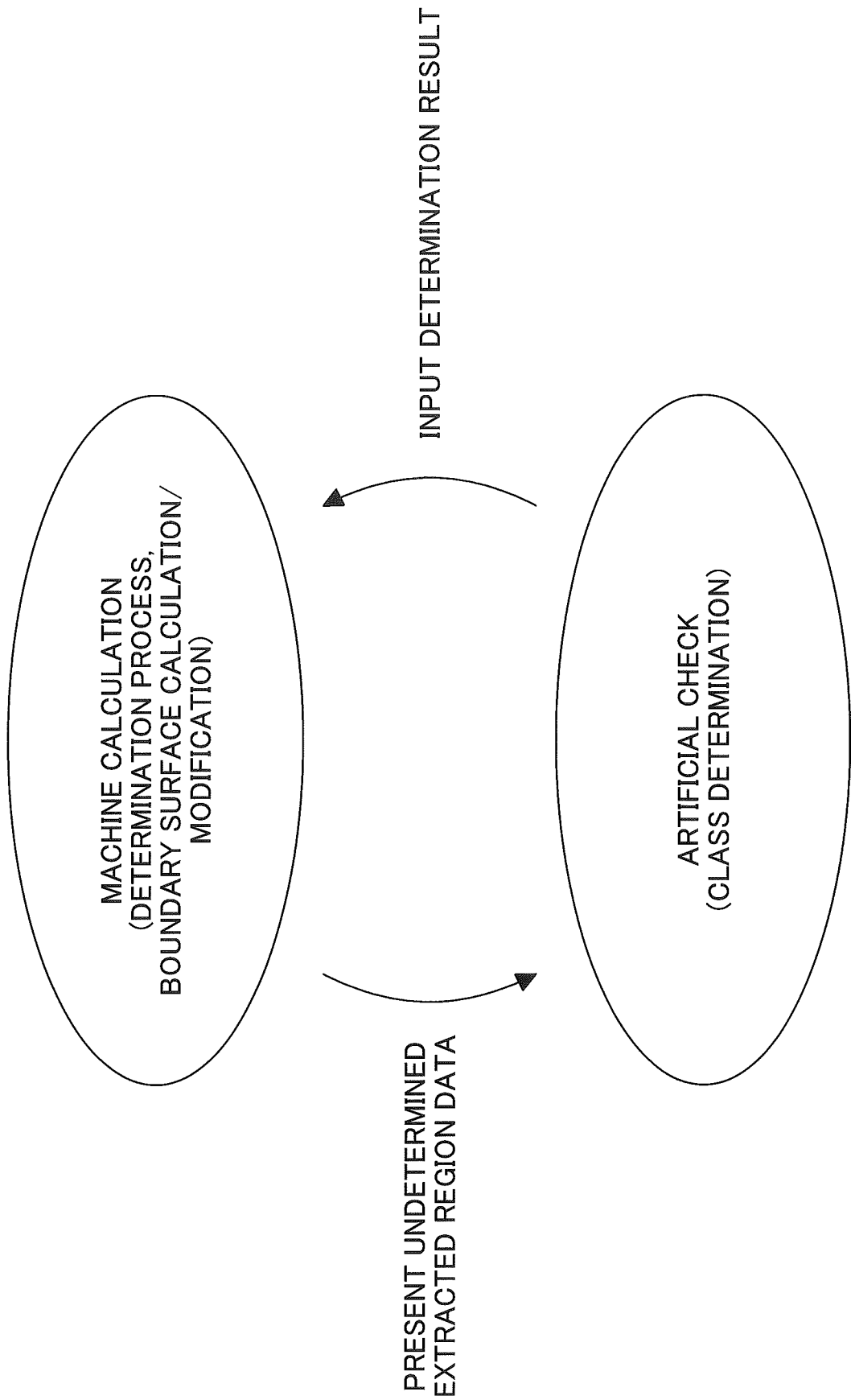
FIG. 5 is a drawing illustrating a flow of a process of generating boundary surfaces.

Next, a flow of a process of generating boundary surfaces performed by the case data generation support unit 121-1 will be described. FIG. 5 is a drawing illustrating the flow of the process of generating boundary surfaces.

As illustrated in FIG. 5, the process of generating boundary surfaces includes a phase of calculating boundary surfaces by using a learning model such as a SVM, and based on the calculated boundary surface, determining classes of extracted region data with unknown classes. The process of generating boundary surfaces also includes a phase of checking, by a doctor, a result obtained by the class determination process using the learning model, and inputting the determination result. The boundary surfaces are generated by alternately repeating these phases.

Specifically, based on the boundary surfaces calculated by using the learning model, the case data generation support unit 121-1 performs the class determination process for determining classes of extracted region data that is unknown as to whether tumor regions are included. Subsequently, the case data generation support unit 121-1 presents undetermined extracted region data to a doctor. A method of presenting undetermined extracted region data to a doctor will be described later.

Based on the presented data, the doctor checks the undetermined extracted region data, which is not yet determined as either the class α or the class β, determines a class, and inputs a determination result into the case data generation support unit 121-1.

The case data generation support unit 121-1 receives the determination result by the doctor, and modifies the boundary surfaces such that the extracted region data whose class has been determined by the doctor is classified into a class corresponding to the determination result by the doctor.

The case data generation support unit 121-1 performs the class determination process for determining the undetermined extracted region data again based on the modified boundary surfaces, and presents the undetermined extracted region data to the doctor. By repeatedly performing presenting undetermined extracted region data, determining a class, and modifying the boundary surfaces, final versions of the boundary surfaces are generated.

Figure 6:
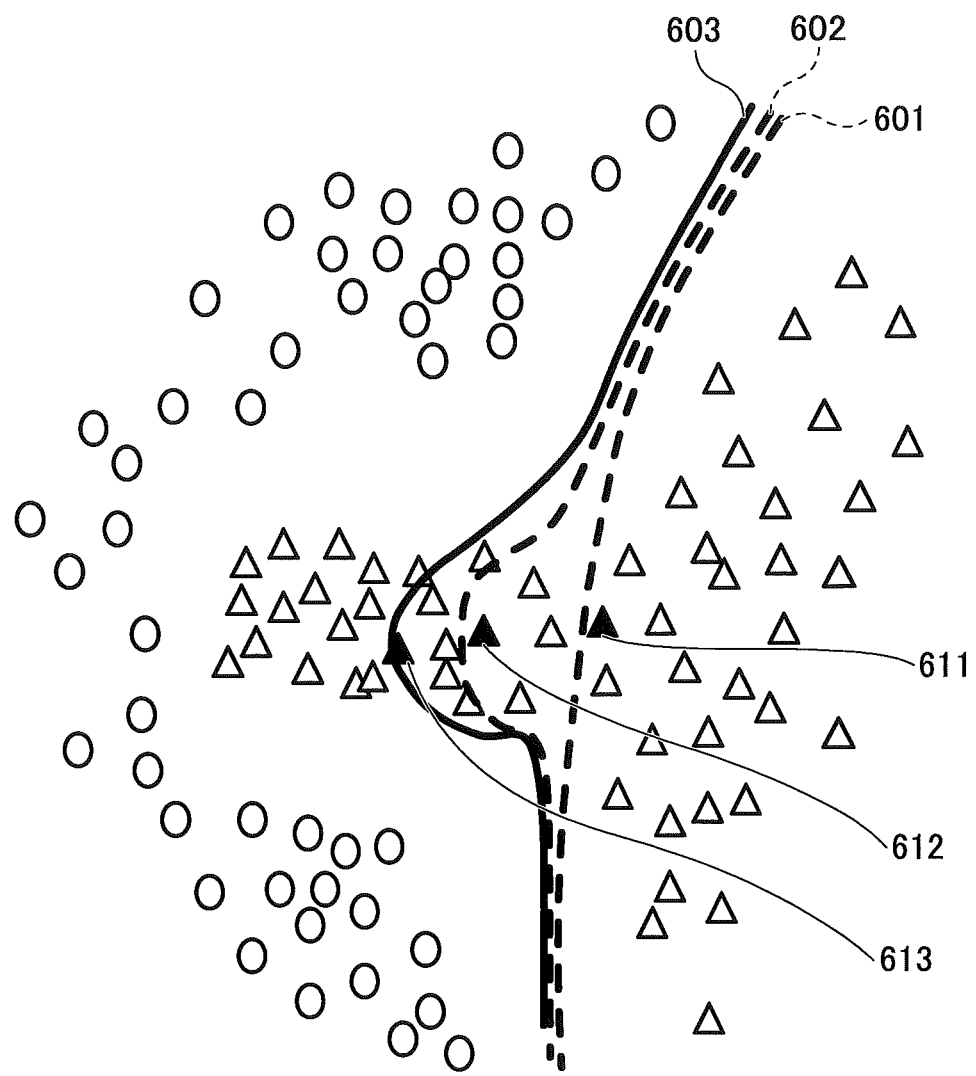
FIG. 6 is a drawing illustrating a conventional modification method used in the process of generating boundary surfaces.

Next, a conventional modification method used in the process of generating boundary surfaces will be described. FIG. 6 is a drawing illustrating the conventional modification method used in the process of generating boundary surfaces. In FIG. 6, circles "○" and triangles "△" indicate distribution of extracted region data in a feature space. Both the circles and triangles represent undetermined extracted region data, but are separately illustrated for convenience of explanation. The circles represent extracted region data that is to be determined as belonging to the class α and the triangles represent extracted region data that is to be determined as belonging to the class β.

A decision surface 601 represents an intermediate plane between a boundary surface indicating a boundary of the class α and a boundary surface indicating a boundary of the class β used in the first round of the class determination process using a learning model.

In the conventional modification method, extracted region data 611 ("▲" illustrated in FIG. 6) closest to the decision surface 601 is presented to a doctor. The doctor determines whether the presented extracted region data 611 is either extracted region data to be determined as belonging to the class α or extracted region data to be determined as belonging to the class β. After the boundary surfaces are modified such that a determination result by the doctor is applied, the learning model performs the second round of the class determination process.

A decision surface 602 represents an intermediate plane between the boundary surface indicating the boundary of the class α and the boundary surface indicating the boundary of the class β used in the second round of the class determination process using the learning model. By applying the determination result by the doctor regarding the extracted region data 611, the decision surface 602 has moved to the left.

In the conventional modification method, an extracted region data 612 ("▲" illustrated in FIG. 6) closest to the modified decision surface 602 is presented to the doctor. The doctor determines whether the presented extracted region data 612 is either extracted region data to be determined as belonging to the class α or extracted region data to be determined as belonging to the class β. In this example, it is assumed that the extracted region data 612 is determined as belonging to the class β. After the boundary surfaces are modified such that the determination result by the doctor is applied, the learning model performs the third round of the class determination process.

A decision surface 603 represents an intermediate plane between the boundary surface indicating the boundary of the class α and the boundary surface indicating the boundary of the class β used in the third round of the class determination process using the learning model. By applying the determination result by the doctor regarding the extracted region data 612, the decision surface 603 has further moved to the left.

In the conventional modification method, an extracted region data 613 ("▲" illustrated in FIG. 6) closest to the modified decision surface 603 is presented to the doctor.

In this way, the extracted region data closest to the modified decision surface 603 is presented to the doctor in the conventional modification method. Therefore, the decision surface moves a small distance. Namely, until the decision surface moves to a proper position, the steps of presenting extracted region data and determining the presented extracted region data by the doctor need to be repeatedly performed.

Conversely, when extracted region data farthest from the decision surface is presented to the doctor and a class to which the extracted region data belongs is determined by the doctor, the number of times that extracted region data is presented and determined by the doctor can be reduced. Therefore, the image analysis apparatus 121 according to the first embodiment is configured to present extracted region data farthest from a decision surface such that a doctor can identify the extracted region data and determines a class to which the extracted region data belongs.

Figure 7:
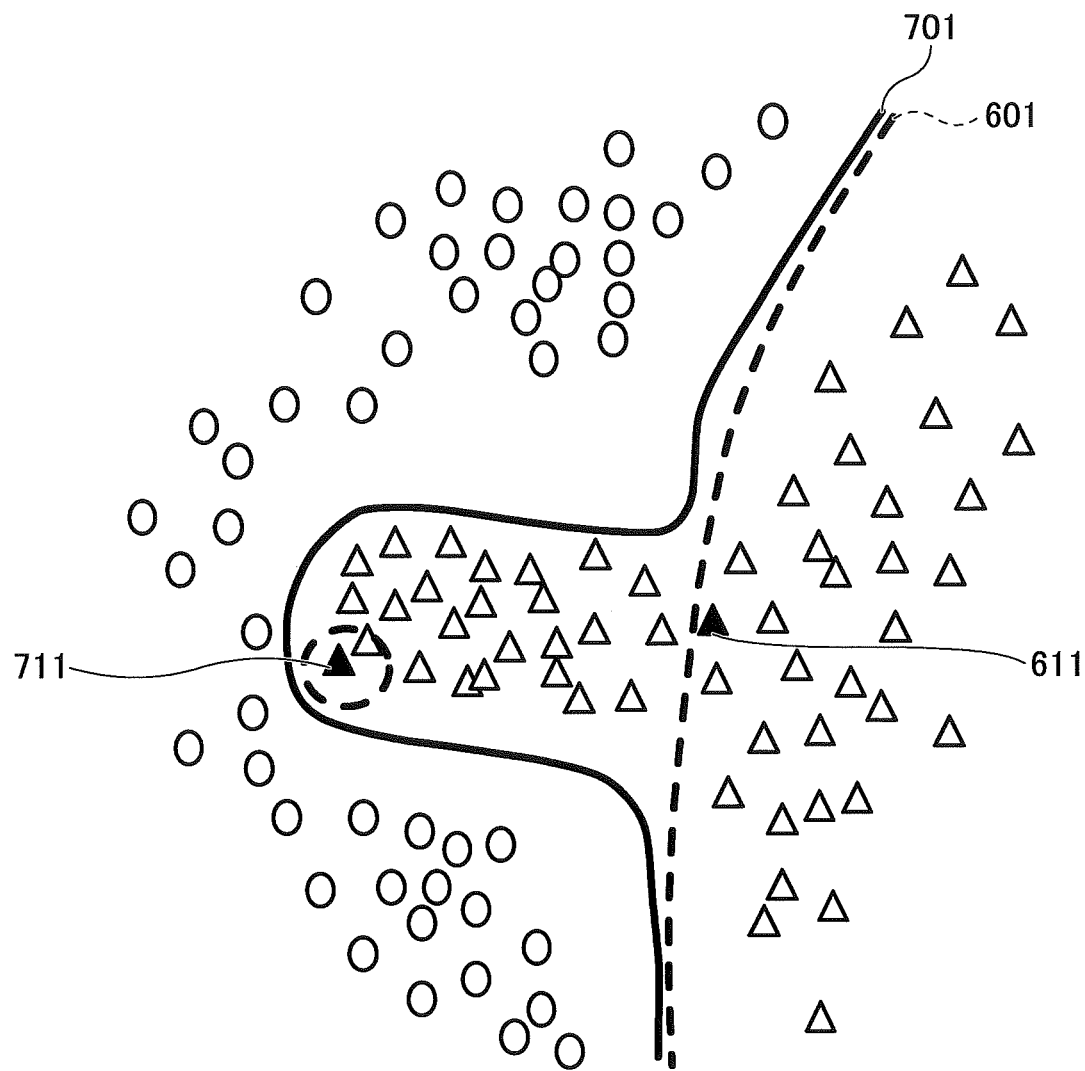
FIG. 7 is a drawing illustrating a modification method used in the process of generating boundary surfaces and performed by the image analysis apparatus according to a first embodiment.

FIG. 7 is a drawing illustrating a modification method used in the process of generating boundary surfaces and performed by the image analysis apparatus according to the first embodiment. In FIG. 7, a decision surface 601 represents an intermediate plane between a boundary surface indicating a boundary of the class α and a boundary surface indicating a boundary of the class R used in the first round of the class determination process using the learning model.

In the modification method performed by the image analysis apparatus 121 according to the first embodiment, the following extracted region data is presented in a recognizable way to a doctor.

Data located on the opposite side of the decision surface 601 when viewed from extracted region data 611 closest to the decision surface 601, Data to be determined as the same class as a class of the extracted region data 611, and Data located at a position farthest from the decision surface 601.

In the example of FIG. 7, extracted region data 711 ("▲" illustrated in FIG. 7) is presented in a recognizable way by a doctor, allowing the doctor to input a determination result of a class of extracted region data 711. Further, after the boundary surfaces are modified by applying the determination result of the extracted region data 711 input by the doctor, the second class determination process using the learning model is performed.

A decision surface 701 represents an intermediate plane between the boundary surface indicating the boundary of the class α and the boundary surface indicating the boundary of the class β used in the second round of the class determination process using the learning model. By applying the determination result by the doctor regarding the extracted region data 711, the decision surface 701 has greatly moved to the left.

Namely, the extracted region data 711 can be regarded as extracted region data having a highly enhanced effect in terms of determination accuracy in modifying the boundary surfaces. Therefore, by presenting the extracted region data 711 in a recognizable way to the doctor, the number of times the extracted region data 711 is presented and determined by the doctor can be reduced.

In the following, as an example of the method of presenting undetermined extracted region data whose classes are not determined, a method of presenting undetermined extracted region data such as extracted region data 711 in a recognizable way to the doctor will be examined below.

As described above, in general, boundary surfaces and a decision surface are high-dimensional surfaces. In a high-dimensional feature space, it is practically difficult for the doctor to recognize the extracted region data 711 located at the position farthest from the decision surface.

First, an example in which extracted region data is projected on a two-dimensional feature plane that is easily recognizable by the doctor will be examined. FIGS. 8A and 8B are graphs for explaining a problem with a method of presenting undetermined extracted region data. In FIGS. 8A and 8B, circles and triangles indicate distribution of undetermined extracted region data. A feature space 810 indicates a three-dimensional feature space including feature quantities 1 through 3. A feature space 820 indicates a two-dimensional feature plane including the feature quantities 1 and 2 (namely, the feature space 820 indicates that the distribution of the undetermined extracted region data is projected on the plane formed by an axis of the feature quantity 1 and an axis of the feature quantity 2).

As illustrated in the feature space 820 of FIG. 8B, when the distribution of the extracted region data is projected on the two-dimensional feature plane, a distance relationship between each of the extracted region data is not stored, making it more difficult to recognize the farthest extracted region data from the decision surface.

Therefore, in the case of a feature space using feature quantities as indexes to define boundary surfaces, it is difficult to recognize a positional relationship between a decision surface and each of extracted region data even if the number of dimensions is reduced. Thus, in the first embodiment, each of distribution of extracted region data is projected on a two-dimensional plane that uses indexes different from the feature quantities to define boundary surfaces.

Figure 9:
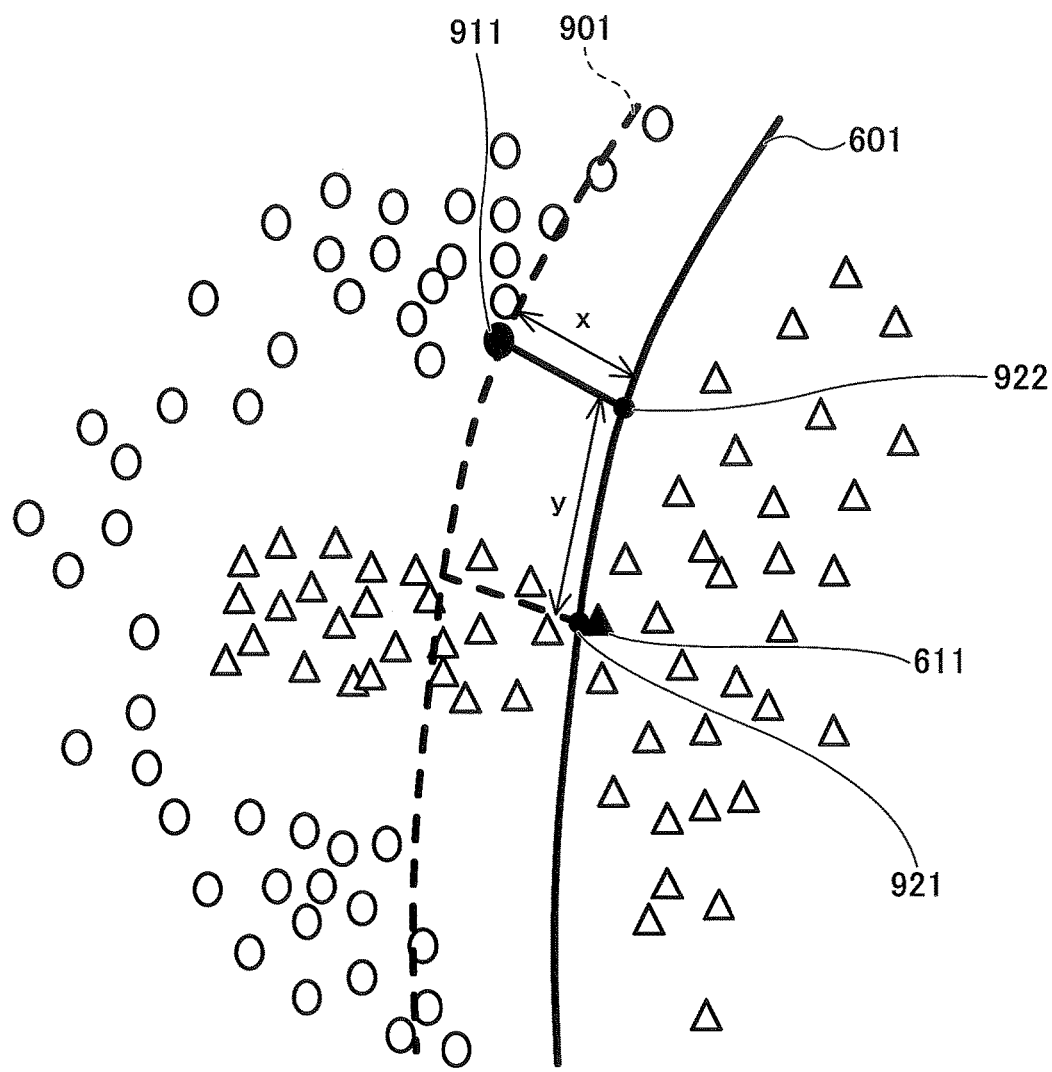
FIG. 9 is a drawing illustrating indexes used in the method of presenting undetermined extracted region data.

FIG. 9 is a drawing illustrating indexes used in the method of presenting undetermined extracted region data according to the first embodiment. A decision surface 601 in FIG. 9 is the same as the decision surface 601 in FIG. 7. Namely, similarly to FIG. 7, the decision surface 601 is an intermediate plane calculated based on a boundary surface of the class α and a boundary surface of the class β used in the first round of the class determination process using the learning model.

An extracted region data 611 in FIG. 9 is the same as the extracted region data 611 in FIG. 6, and is the closest extracted region data to the decision surface 601. An index x and an index y are indexes each indicating a position of each of extracted region data. In the example of FIG. 9, the indexes indicate a position of extracted region data 911.

To be more specific, the index x indicates a distance between the extracted region data 911 and a point of intersection 922, which is the point between the decision surface 601 and a straight line passing through the extracted region data 911 and approximately orthogonal to the decision surface 601.

Also, the index y indicates a distance between the position of the point of intersection 922 and the position of a point 921. The position of the point 921 is obtained by moving the point of intersection 922 along the decision surface 601 to a point closest to the extracted region data 611 on the decision surface 601. When a group of extracted region data distributed in the feature space is classified into two classes by the decision surface 601, the position of the point 921 is determined based on the position of the extracted region data 611 that is closest to the decision surface 601 and belongs to one of the two classes of the group of extracted region data.

In the first embodiment, the index x and the index y are used to present undetermined extracted region data to a doctor. When the position of the point 921 is regarded as a reference value in the feature space, the index x and the index y are indexes each indicating a degree of separation of each of extracted region data relative to the reference value. Further, instead of using the point 921, the position of the extracted region data 611 may be used as the reference value.

Now, a relationship between the index x and extracted region data will be described. FIGS. 10A through 10C are graphs for explaining the relationship between the index x and undetermined extracted region data. In a graph 1010 and a graph 1020, a horizontal axis (an x-axis) represents the index x and a vertical axis (a y-axis) represents the number of pieces of undetermined extracted region data for each value of the index x.

The graph 1010 represents the number of pieces of undetermined extracted region data distributed on the opposite side of the decision surface 601 when viewed from the extracted region data 611 closest to the decision surface 601. Further, the number of pieces of undetermined extracted region data is illustrated as divided into the number of pieces of extracted region data to be determined as belonging to the class α and the number of pieces of extracted region data to be determined as belonging to the class β.

The graph 1020 represents the number of pieces of undetermined extracted region data distributed inside the decision surface 601 when viewed from the extracted region data 611 closest to the decision surface 601.

As can be seen from the graph 1020, the undetermined extracted region data distributed inside the decision surface 601 when viewed from the extracted region data 611 includes only extracted region data belonging to the same class as that (the class β) of the extracted region data 611.

Conversely, as can be seen from the graph 1010, the undetermined extracted region data distributed on the opposite side of the decision surface 601 when viewed from the extracted region data 611 includes both extracted region data to be determined as belonging to the class α and extracted region data to be determined as belonging to the class β.

Therefore, according to the graph 1010 and the graph 1020, it is found that the decision surface 601 crosses a region where extracted region data to be determined as belonging to the class β is distributed in the feature space.

Further, in FIG. 10C, a graph 1030 is obtained by flipping the graph 1010 about the y-axis and combining with the graph 1020. In the graph 1030, a region I indicates a region on the opposite side of the decision surface 601 when viewed from the extracted region data 611. Also, a region II indicates a region inside the decision surface 601 when viewed from the extracted region data 611.

According to the graph 1030, in order to avoid the decision surface 601 from crossing the region where the extracted region data to be determined as belonging to the class β is distributed in the feature space, the decision surface 601 may be adjusted to become closer to a dotted line 1031. Namely, among the undetermined extracted region data to be determined as belonging to the class β, the doctor may determine a class of extracted region data that is included in a hatched region 1032 and is closer to the dotted line 1031.

However, the extracted region data in the hatched region 1032 includes both extracted region data to be determined as belonging to the class α and extracted region data to be determined as belonging to the class β.

Accordingly, in the first embodiment, extracted region data to be determined as belonging to the class α and extracted region data to be determined as belonging to the class β are separated in consideration of the following characteristics of extracted region data distributed in the vicinity of the extracted region data 611 when viewed in a direction along the decision surface 601.

When extracted region data distributed in the vicinity of the extracted region data 611 is viewed in the direction along the decision surface 601, extracted region data to be determined as belonging to the class β is distributed at positions close to the extracted region data 611.

When extracted region data distributed in the vicinity of the extracted region data 611 is viewed in the direction along the decision surface 601, extracted region data to be determined as belonging to the class α is distributed at positions away from the extracted region data 611.

Figure 11:
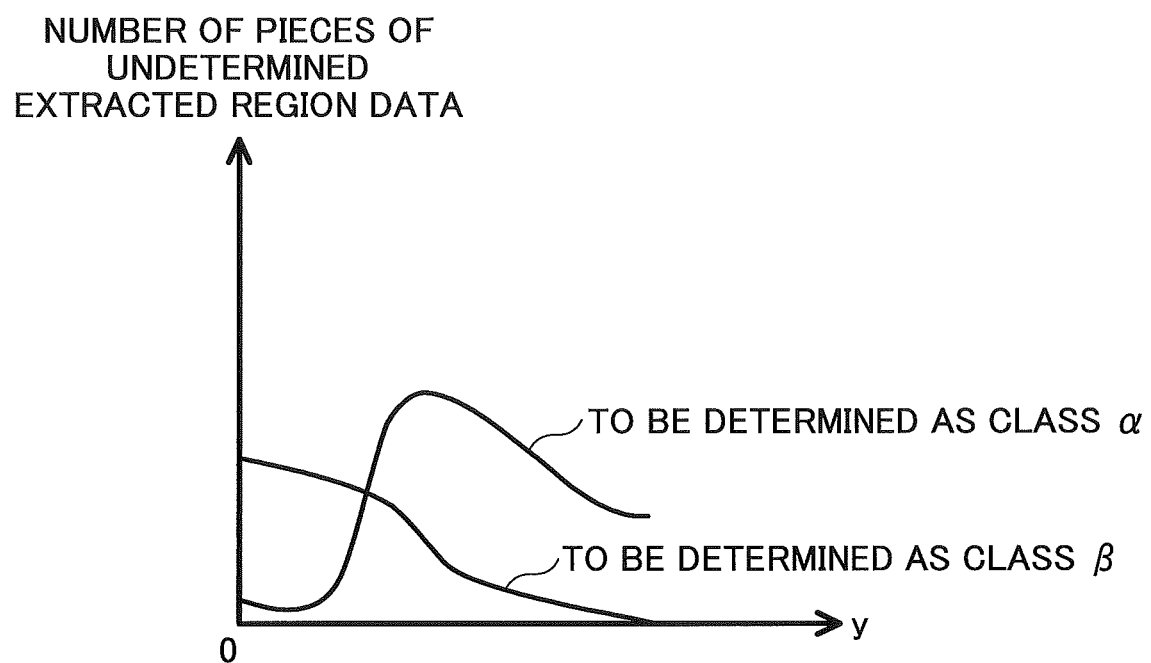
FIG. 11 is a graph for explaining a relationship between an index y and undetermined extracted region data.

FIG. 11 is a graph illustrating the above-described characteristics and is also a graph for explaining a relationship between the index y and undetermined extracted region data.

As illustrated in FIG. 11, when the index y is small (namely, at positions close to the extracted region data 611 when viewed in the direction along the decision surface 601), extracted region data to be determined as belonging to the class β is distributed. Conversely, when the index y is large (namely, at positions away from the extracted region data 611 when viewed in the direction along the decision surface 601), extracted region data to be determined as belonging to the class α is distributed.

The above-described characteristics are due to the decision surface 601 that crosses the region where extracted region data to be determined as belonging to the class β is distributed.

By plotting undetermined extracted region based on the direction along the decision surface 601 (namely, along the index y), extracted region data included in the hatched region 1032 can be displayed as grouped into the corresponding classes.

As is clear from the description of FIGS. 10A through 10C and FIG. 11, the use of the index x and the index y brings about the following.

By plotting undetermined extracted region data to be determined as belonging to the class β by using the index x, extracted region data distributed at positions away from the extracted region data 611 can be presented in an easily recognizable way to a doctor.

By plotting undetermined extracted region data by using the index y, extracted region data to be determined as belonging to the class β can be presented to the doctor without being mixed with extracted region data to be determined as belonging to the class α.

In the first embodiment, a two-dimensional plane with the index x and the index y approximately orthogonal to each other is formed. By using the two-dimensional plane, undetermined extracted region data is presented.

Figure 12:
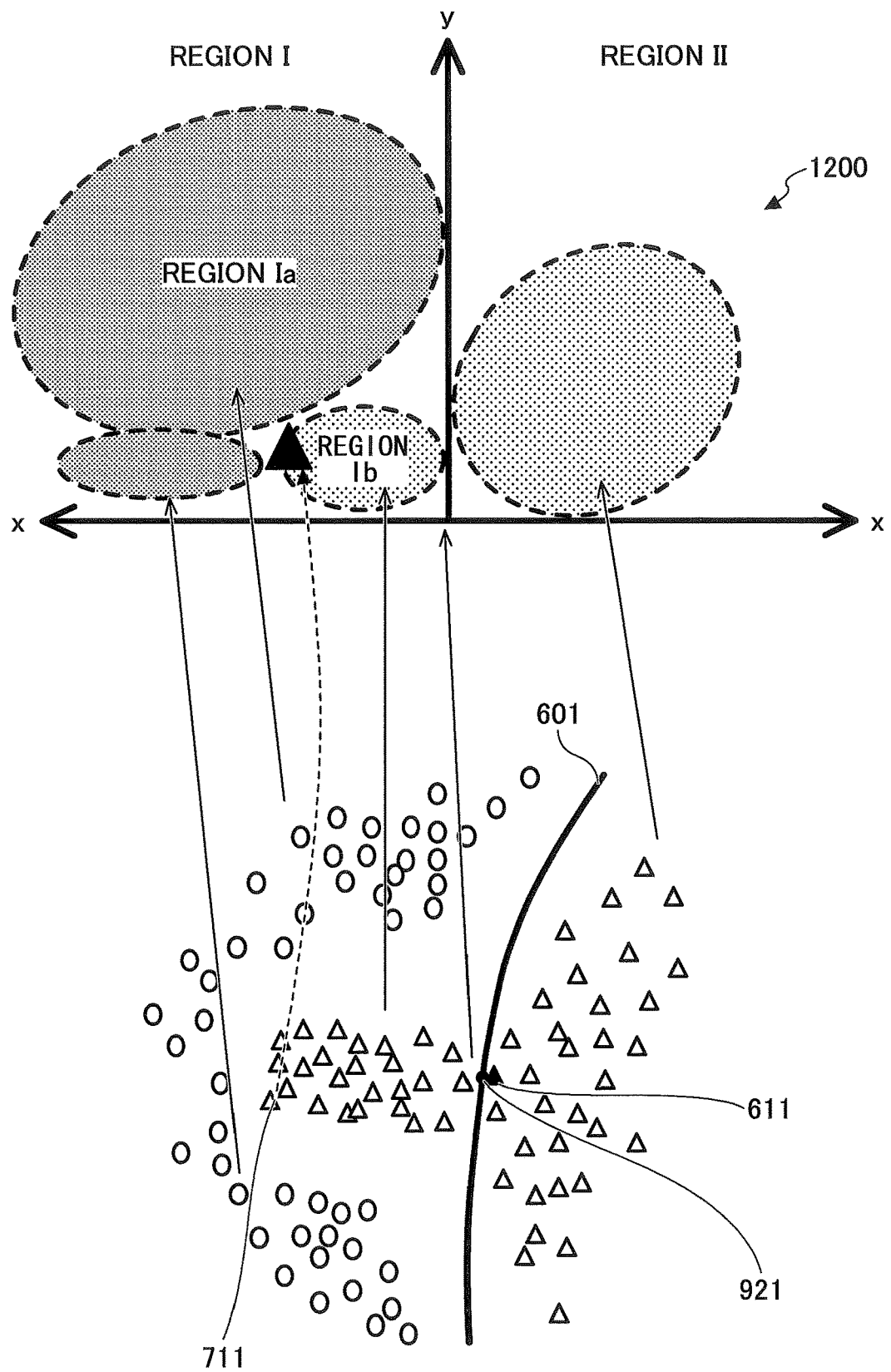
FIG. 12 is a graph for explaining the method of presenting undetermined extracted region data according to a first embodiment.

FIG. 12 is a graph for explaining the method of presenting undetermined extracted region data according to the first embodiment. As illustrated in FIG. 12, in the method of presenting undetermined extracted region data according to the first embodiment, undetermined extracted region data is presented on a two-dimensional plane 1200 with the horizontal axis being the index x and the vertical axis being the index y. Further, a point of intersection of the horizontal axis and the vertical axis indicates the position of the point 921 closest to the extracted region data 611 on the decision surface 601.

In the two-dimensional plane 1200, extracted region data (mainly indicated by circles) distributed on the opposite side of the decision surface 601 when viewed from the extracted region data 611 is plotted in the region I. Also, in the two-dimensional plane 1200, extracted region data (indicated by triangles) distributed inside the decision surface 601 when viewed from the extracted region data 611 is plotted in the region II.

Further, the region I includes a part of the extracted region data indicated by the triangles, in addition to the extracted region data indicated by the circles. However, in the two-dimensional plane 1200 using the index x and the index y, a region Ia in which the extracted region data indicated by the circles is plotted is separated from a region Ib in which the extracted region data indicated by the triangles is plotted.

Accordingly, by visually checking the two-dimensional plane 1200, the doctor can easily recognize the extracted region data 711 as extracted region data having a highly enhanced effect in terms of determination accuracy in modifying the boundary surfaces when the following conditions are met.

Data located on the opposite side of the decision surface 601 when viewed from the extracted region data 611 closest to the decision surface 601.

Data to be determined as the same class as that of the extracted region data 611.

Data located at a position farthest from the decision surface 601.

Figure 13:
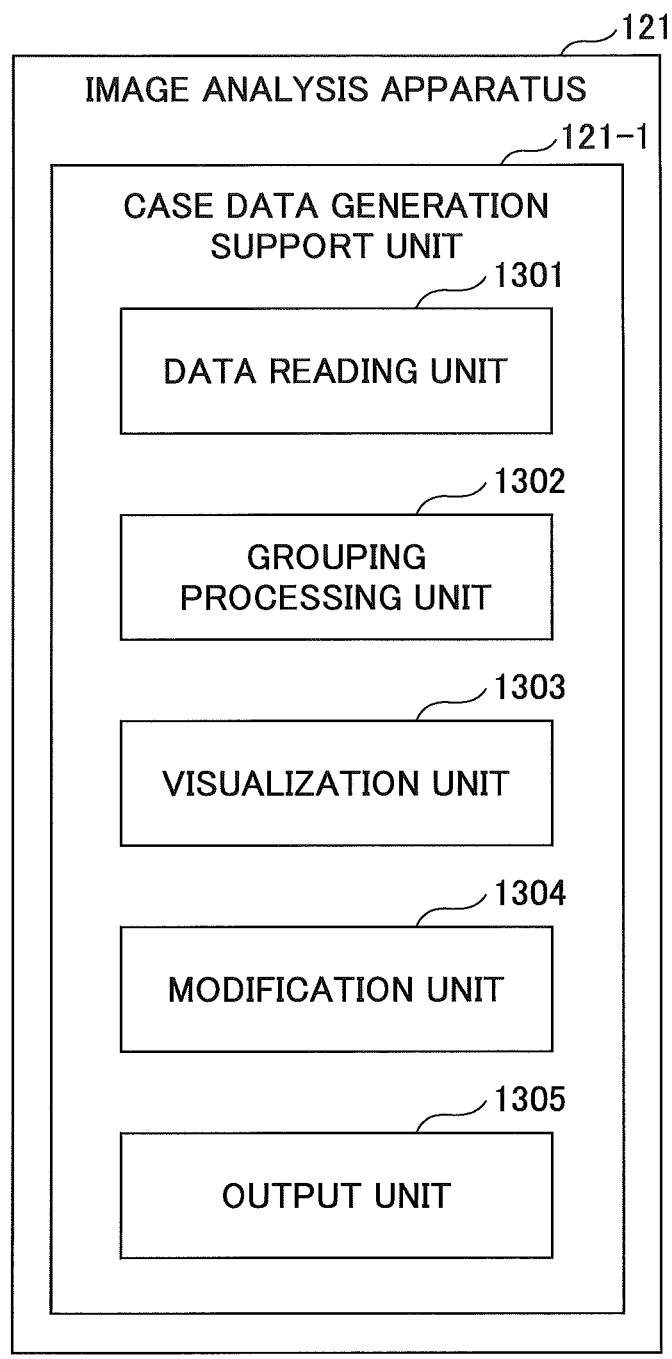
FIG. 13 is a drawing illustrating an example of a functional configuration of the image analysis apparatus.

Next, a functional configuration of the case data generation support unit 121-1 of the image analysis apparatus 121 that performs the above-described presentation method will be described. FIG. 13 is a drawing illustrating an example of the functional configuration of the image analysis apparatus.

As illustrated in FIG. 13, the case data generation support unit 121-1 of the image analysis apparatus 121 includes a data reading unit 1301, a grouping processing unit 1302, a visualization unit 1303, a modification unit 1304, and an output unit 1305.

The data reading unit 1301 reads extracted region data stored in the CT image data storage DB 114-1. When boundary surfaces are calculated by using the learning model, the data reading unit 1301 reads extracted region data that is known to include tumor regions (extracted region data with known classes). Also, when the boundary surfaces are modified, the data reading unit 1301 reads extracted region data that is unknown as to whether tumor regions are included (extracted region data with unknown classes).

The grouping processing unit 1302 includes the learning model such as the SVM, and calculates boundary surfaces indicating a boundary of each class, based on extracted region data with known classes that are extracted by the data reading unit 1301. Further, the grouping processing unit 1302 calculates a decision surface that is an intermediate plane between the calculated boundary surfaces of the classes, and indicates the decision surface to the visualization unit 1303. Further, the grouping processing unit 1302 performs the class determination process for the extracted region data extracted by the data reading unit 1301, and indicates undetermined extracted region data to the visualization unit 1303.

The visualization unit 1303 presents the undetermined extracted region data indicated by the grouping processing unit 1302 to a doctor. When the visualization unit 1303 presents the undetermined extracted region data to the doctor, the visualization unit 1303 extracts N number of pieces of extracted region data closest to the decision surface 601. Each of the N number of pieces of extracted region data is plotted on a two-dimensional plane 1200 along with n number of undetermined extracted region data in the vicinity, and the created dimensional planes 1200 are presented to the doctor.

In each of N number of dimensional planes 1200, the doctor selects extracted region data located farthest from the decision surface 601 (namely, extracted region data having a highly enhanced effect in terms of determination accuracy in modifying the boundary surfaces), and the modification unit 1304 receives the extracted region data selected by the doctor. Subsequently, the doctor determines a class of the selected extracted region data, and the modification unit 1304 receives the determination result by the doctor. Further, the modification unit 1304 indicates the received determination result to the grouping processing unit 1302. The grouping processing unit 1302 causes the extracted region data, whose class has been indicated by the modification unit 1304, to be included in extracted region data with known classes, and re-calculates the boundary surfaces. Namely, the grouping processing unit 1302 re-calculates the boundary surfaces by applying the determination result by the doctor.

The output unit 1305 registers, in the case data retrieval DB 114-2, parameters defining the boundary surfaces calculated by the grouping processing unit 1302. Further, the output unit 1305 registers, in the information item "image data" of the case data retrieval DB 114-2, the extracted region data determined by the grouping processing unit 1302.

Figure 14:
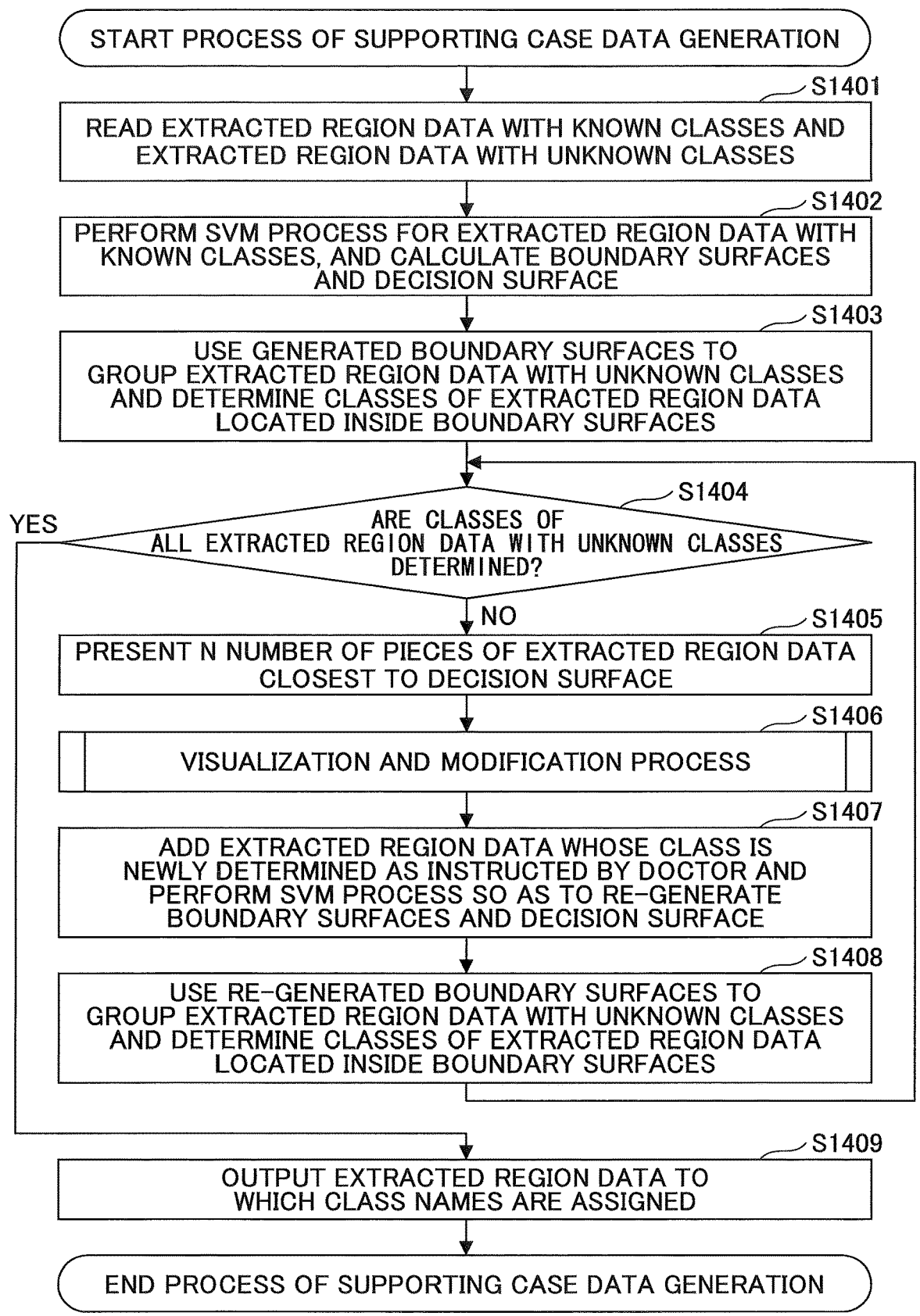
FIG. 14 is a flowchart illustrating a process of supporting case data generation.

Next, a flow of a process of supporting case data generation performed by the case data generation support unit 121-1 of the image analysis apparatus 121 will be described. FIG. 14 is a flowchart illustrating the process of supporting case data generation.

In step S1401, the data reading unit 1301 reads, as extracted region data with known classes, extracted region data that is stored in the CT image data storage DB 114-1 and is known to include tumor regions. Also, the data reading unit 1301 reads, as extracted region data with unknown classes, extracted region data that is stored in the CT image data storage DB 114-1 and is unknown as to whether tumor regions are included.

In step S1402, the grouping processing unit 1302 performs the SVM process for the extracted region data with known classes so as to calculate a boundary surface indicating a boundary of the class α and a boundary surface indicating a boundary of the class β. Also, the grouping processing unit 1302 calculates a decision surface based on the calculated boundary surface indicating the boundary of the class α and the calculated boundary surface indicating the boundary of the class β.

In step S1403, the grouping processing unit 1302 uses the boundary surfaces calculated in step 1402 to determine classes of the extracted region data with unknown classes read in step S1401. Specifically, among the extracted region data with unknown classes, the grouping processing unit 1302 determines classes of extracted region data located inside the boundary surfaces. More specifically, the grouping processing unit 1302 determines classes of the extracted region data located inside the boundary surface indicating the boundary of the class α as class α. Conversely, the grouping processing unit 1302 determines classes of the extracted region data located inside the boundary surface indicating the boundary of the class β as class β.

In step S1404, the grouping processing unit 1302 determines whether classes of all the extracted region data with unknown classes are determined.

In step S1404, when it is determined that there is remaining extracted region data whose class is not yet determined, the process proceeds to step S1405. In step S1405, of the undetermined extracted region data, the grouping processing unit 1302 causes N number of pieces of extracted region data closest to the decision surface calculated in step S1402 to be displayed on the display apparatus 122.

In step S1406, based on each of the N number of pieces of extracted region data displayed on the display apparatus 122, the visualization unit 1303 causes each of the N number of pieces of extracted region data to be plotted and visualized on a two-dimensional plane 1200 along with n number of pieces of extracted region data located in the vicinity. Further, after extracted region data is selected and a class of the extracted region data is determined by a doctor, the modification unit 1304 receives the result of the class determined by the doctor. Visualization and modification process (step S1406) will be described later in detail.

In step S1407, the grouping processing unit 1302 causes the extracted region data whose class is newly determined in step S1406 to be included in the extracted region data with known classes. Subsequently, the grouping processing unit 1302 performs the SVM process so as to re-calculate the boundary surfaces and the decision surface.

In step S1408, the grouping processing unit 1302 uses the boundary surfaces re-calculated in step S1407 to determine classes of the extracted region data with unknown classes read in step S1401. Specifically, among the extracted region data with unknown classes, the grouping processing unit 130 determines classes of extracted region data located inside the boundary surfaces, and causes the process to return to step 1404.

In step S1404, the grouping processing unit 1302 determines whether classes have been determined for all the extracted region data with unknown classes. In step S1404, when it is determined that there is remaining extracted region data whose class is not determined (no in step S1404), steps S1405 through S1408 are repeated.

Conversely, in step S1404, when it is determined that classes have been determined for all the extracted region data with unknown classes (yes in S1404), the process proceeds to step S1409.

In step S1409, the output unit 1305 outputs extracted region data to which class names are assigned.

Figure 15:
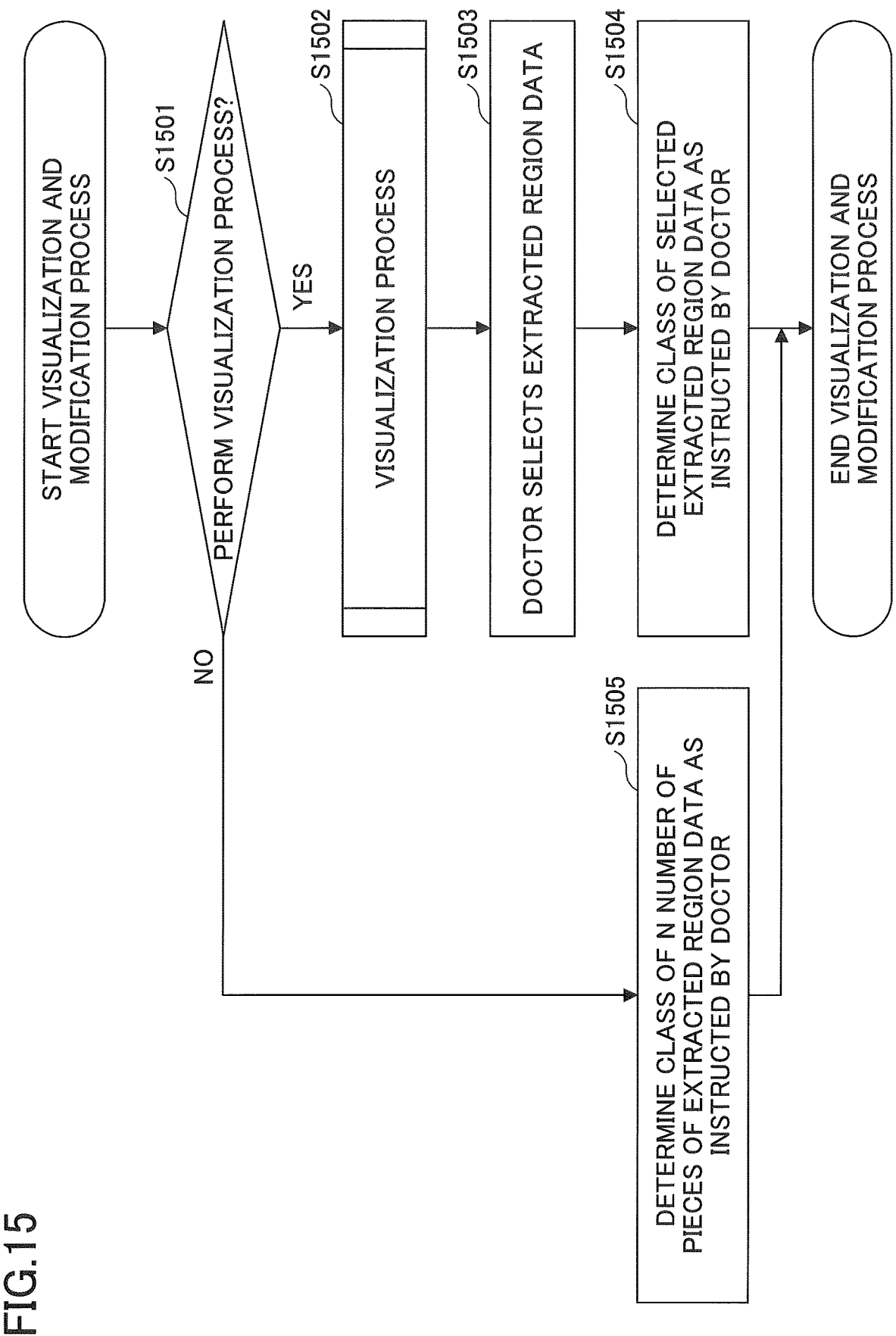
FIG. 15 is a flowchart illustrating a visualization and modification process.

Next, the visualization and modification process (step S1406 of FIG. 14) will be described in detail. FIG. 15 is a flowchart illustrating the visualization and modification process.

In step S1501, the visualization unit 1303 determines whether to perform a visualization process for visualizing each of the N number of pieces of the extracted region data presented in step S1405. When an instruction to perform visualization is input by the doctor (yes in step S1501), the visualization unit 1303 determines to perform the visualization process and causes the process to proceed to step S1502. Conversely, when an instruction not to perform the visualization process is input by the doctor (no in step S1501), the visualization unit 1303 determines not to perform visualization and causes the process to proceed to step S1505.

In step S1502, the visualization unit 1303 performs the visualization process. The visualization process will be described later in detail.

In step S1503, after the doctor selects extracted region data from the n number of pieces of extracted region data located in the vicinity of each of the N number of pieces of extracted region data visualized by the visualization process in step S1502, the visualization unit 1303 identifies the selected extracted region data by the doctor.

In step S1504, after the doctor determines the class of the extracted region data identified in step S1503, the modification unit 1304 identifies the class determined by the doctor. Accordingly, the class of the extracted region data selected by the doctor is determined.

Conversely, in step S1505, the modification unit 1304 identifies a class of each of the N number of pieces of extracted region data determined by the doctor. Accordingly, the class of each of the N number of pieces of extracted region data is determined.

Figure 16:
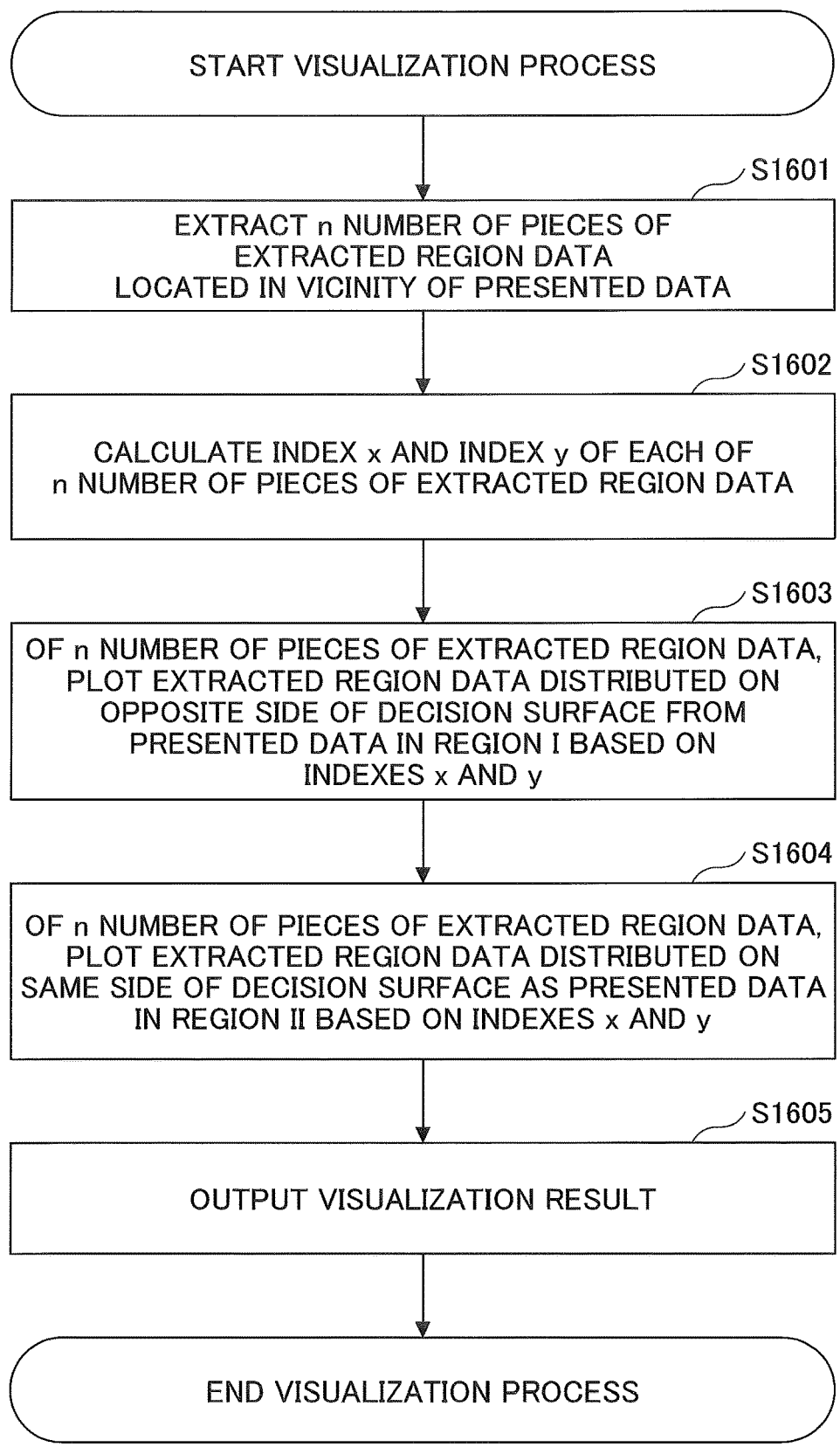
FIG. 16 is a first flowchart of a visualization process.

Next, the visualization process (step S1502 of FIG. 15) will be described in detail. FIG. 16 is a first flowchart of the visualization process. The visualization process illustrated in FIG. 16 is performed for each of the N number of pieces of extracted region data presented in step S1405 (hereinafter referred to as "presented data"). For simplification of explanation, an example in which the visualization process is performed for a single piece of presented data among the N number of pieces of presented data will be described.

In step S1601, the visualization unit 1303 extracts n number of pieces of extracted region data located in the vicinity of the single piece of the presented data.

In step S1602, the visualization unit 1303 calculates an index x and an index y of each of the n number of pieces of extracted region data extracted in step S1601.

In step S1603, of the n number of pieces of extracted region data, the visualization unit 1303 plots, in a region I, extracted region data distributed on the opposite side of the decision surface 601 when viewed from the presented data.

In step S1604, among the n number of pieces of extracted region data, the visualization unit 1303 plots, in a region II, extracted region data distributed inside the decision surface 601 when viewed from the presented data.

In step S1605, the visualization unit 1303 causes a visualization result of plotting the n number of pieces of extracted region data to be displayed on the display apparatus 122.

Figure 17:
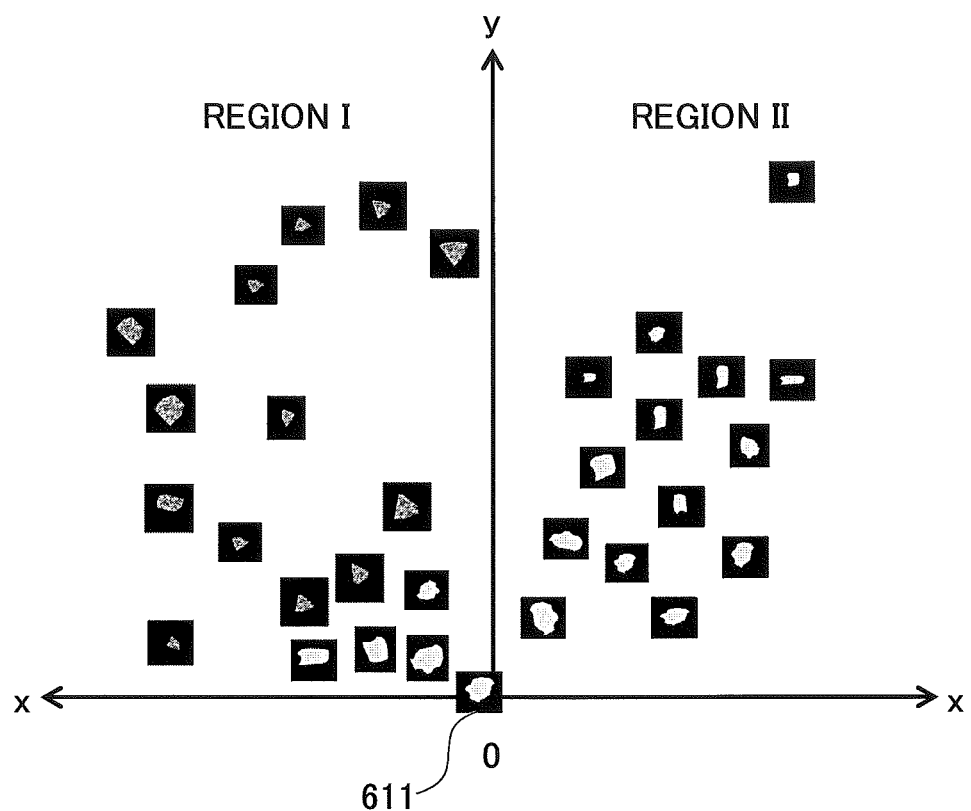
FIG. 17 is a first graph illustrating an example of a visualization result.

FIG. 17 is a first graph illustrating an example of the visualization result. As illustrated in FIG. 17, in the visualization result obtained by the visualization unit 1303, extracted region data to be determined as belonging to the class α and extracted region data to be determined as belonging to the class β can be separately displayed in the region I. Also, in the region I, the extracted region data to be determined as belonging to the class β and distributed at positions away from the decision surface can be easily recognized.

Accordingly, it becomes possible for a doctor to easily select extracted region data having a highly enhanced effect in terms of accuracy in modifying boundary surfaces.

As is clear from the above description, in the image analysis apparatus 121, a decision surface is calculated based on boundary surfaces used to classify a group of extracted region data into two classes, and of the group of extracted region data, pieces of extracted region data are plotted and displayed along at least one axis indicating a distance of each of the pieces of extracted region data relative to the decision surface.

Accordingly, the image analysis apparatus 121 allows a doctor to select data having a highly enhanced effect and for the number of times boundary surfaces are modified to be reduced. Namely, it is possible to support the doctor in modifying the boundary surfaces used to group a plurality of pieces of extracted region data into two classes.

Second Embodiment

In the above-described first embodiment, in the visualization process performed by the visualization unit 1303, extracted region data is plotted by calculating a distance from the decision surface (the index x) and a distance relative to the presented data (the index y). In the present embodiment, a distance from the decision surface (the index x) is calculated, and based on the calculated distance (the index x), extracted region data is plotted. In this case, when pieces of extracted region data have the same distance (the same index x), the pieces of extracted region data overlap each other when displayed at a plotted position. Therefore, in the second embodiment, extracted region data having the substantially same distance as another extracted region data is displayed by being shifted in a direction (y-axis direction) approximately orthogonal to the x-axis direction. In the second embodiment, differences from the first embodiment will be mainly described.

Figure 18:
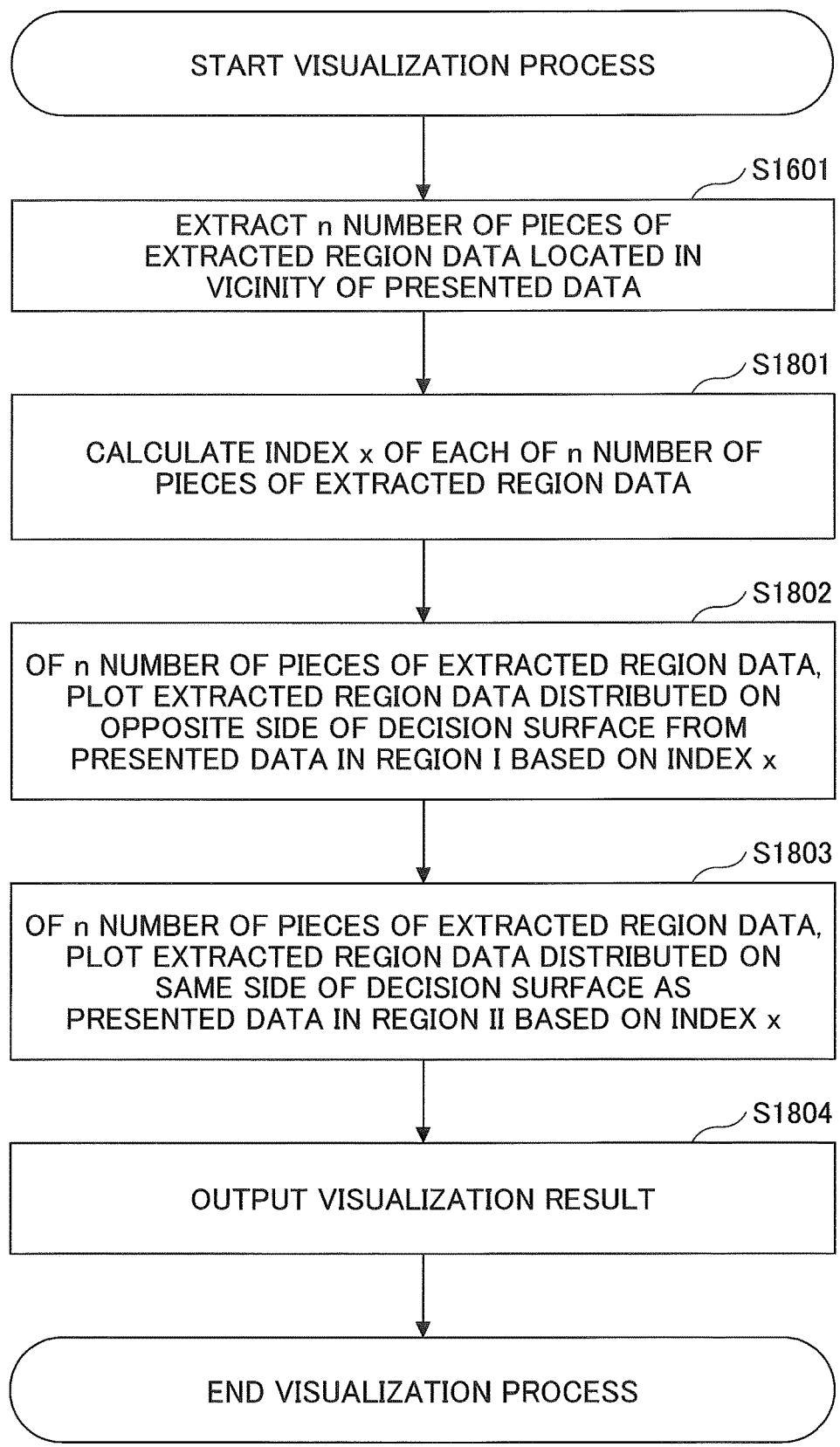
FIG. 18 is a second flowchart of the visualization process.

First, the visualization process (step S1502 of FIG. 15) according to the second embodiment will be described in detail. FIG. 18 is a second flowchart, in the visualization process. As with the first embodiment, in the visualization process illustrated in FIG. 18, the visualization process is performed for each of the N number of pieces of the extracted region data presented in step S1405. For simplification of explanation, an example in which the visualization process is performed for a single piece of presented data will be described below.

In step S1601, the visualization unit 1303 extracts n number of pieces of extracted region data located in the vicinity of the single piece of the presented data.

In step S1801, the visualization unit 1303 calculates an index x of each of the n number of pieces of extracted region data extracted in step S1601.

In step S1802, among the n number of pieces of extracted region data, the visualization unit 1303 plots, in a region I, extracted region data distributed on the opposite side of the decision surface 601 when viewed from the presented data.

At this time, in a case where some of the extracted region data have the same or the substantially same distance (index x) and possibly overlap with each other, the overlapped extracted region data is shifted in a direction approximately orthogonal to the x-axis direction and is displayed by the visualization unit 1303.

In S1803, among the n number of pieces of extracted region data, the visualization unit 1303 plots, in a region II, extracted region data distributed inside the decision surface 601 when viewed from the presented data.

At this time, when some of the extracted region data has the same or the substantially same distance (index x) and possibly overlap each other when displayed, the overlapped extracted region data is shifted in a direction approximately orthogonal to the x-axis direction for display by the visualization unit 1303.

In step S1804 the visualization unit 1303 causes a visualization result of plotting the n number of pieces of extracted region data to be displayed on the display apparatus 122.

Figure 19:
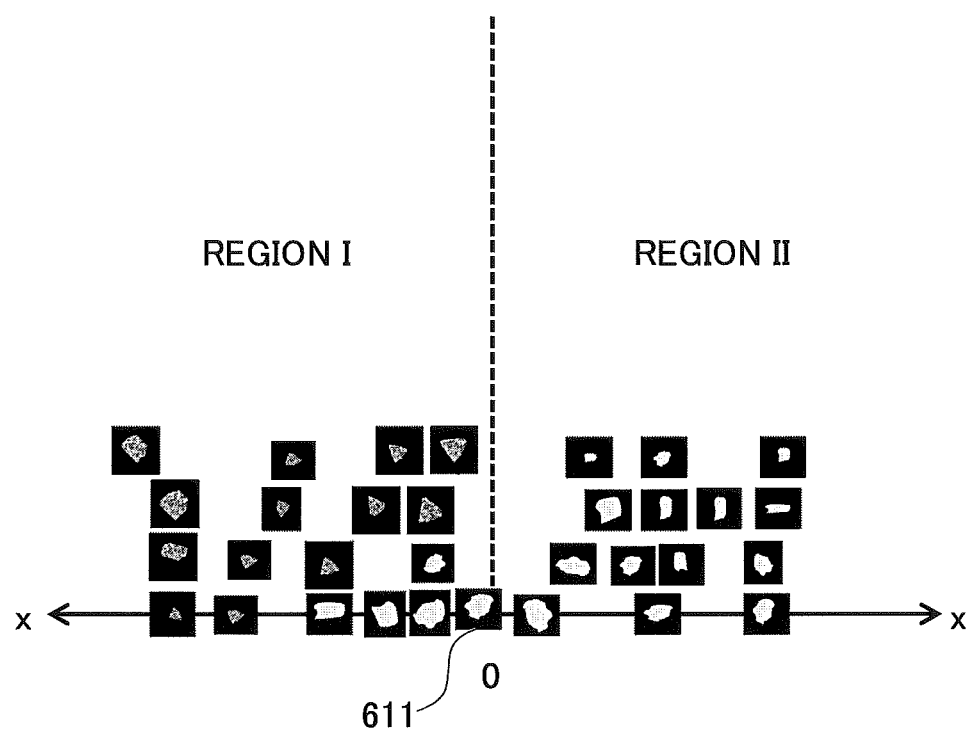
FIG. 19 is a second drawing illustrating an example of a visualization result.

FIG. 19 is a second drawing illustrating an example of the visualization result. As illustrated in FIG. 19, in the visualization result obtained by the visualization unit 1303, extracted region data to be determined as belonging to the class α and extracted region data to be determined as belonging to the class β can be separately displayed in the region I. Also, in the region I, the extracted region data to be determined as belonging to the class β and distributed at positions away from the decision surface can be easily recognized.

Accordingly, it becomes possible for a doctor to easily select extracted region data having a highly enhanced effect in terms of accuracy in modifying boundary surfaces.

As is clear from the above description, in the image analysis apparatus 121, a decision surface is calculated based on boundary surfaces used to classify a group of extracted region data into two classes, and of the group of extracted region data, pieces of extracted region data are plotted and displayed along at least one axis indicating a distance of each of the pieces of extracted region data relative to the decision surface.

Accordingly, the image analysis apparatus 121 allows a doctor to select data having a largely enhanced effect and for the number of times boundary surfaces are modified to be reduced. Namely, it is possible to support the doctor in modifying the boundary surfaces used to group a plurality of pieces of extracted region data into two classes.

According to at least one embodiment, it is possible to support a doctor or other health professional in modifying boundary surfaces used to classify a group of image data into classes.

The present invention is not limited to the configurations described herein, and other elements may be combined with the configurations of the above-described embodiments. These configurations may be modified without departing from the scope of the present invention, and may be appropriately defined according to the application forms.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present invention have been described in detail, it should be understood that the various changes, substitutions, and alterations could be made hereto without departing from the spirit and scope of the invention.

What is claimed is:

1. A non-transitory recording medium having stored therein a program for causing a computer to execute a case data generation support process comprising:
   determining a reference value on a decision surface used for classifying a group of image data represented by a plurality of types of feature quantities into first and second classes in a feature quantity space, based on a feature quantity of a reference image data piece, the reference image data piece being closest to the decision surface in the feature quantity space and determined as belonging to the first class;
   plotting and displaying in a two-dimensional plane pieces of image data extracted from the group of image data, each of the plotted and displayed pieces of image data being distributed along each of two orthogonal axes of the two-dimensional plane in accordance with a degree of separation calculated for each of the pieces of image data relative to the reference value; and
   modifying, upon receiving a single piece of image data identified from among the plotted and displayed pieces of image data in the two-dimensional plane, the decision surface based on the identified single piece of image data;
   wherein the plotted and displayed pieces of image data in the two-dimensional plane include:
   pieces of image data to be determined as belonging to the first class plotted in a first region on an opposite side of the decision surface when viewed from a position of the reference image data piece; and
   pieces of image data to be determined as belonging to the second class plotted in a second region on the opposite side of the decision surface, the second region being visually distinct from the first region.

2. The non-transitory recording medium according to claim 1, wherein the degree of separation calculated for each of the pieces of image data indicates a distance of a position of the piece of image data from the position of the reference image data piece in the two-dimensional plane.

3. The non-transitory recording medium according to claim 1, wherein, in response to a possibility of one of the pieces of image data being overlapped with another of the pieces of image data when plotted and displayed along one axis indicating the degree of separation of each of the pieces of image data relative to the reference value, the one of the pieces of image data is plotted and displayed by being shifted in a direction orthogonal to the one axis.

4. The non-transitory recording medium according to claim 3, wherein the degree of separation of each of the pieces of image data relative to the reference value is a degree of separation in a direction approximately orthogonal to the decision surface.

5. The non-transitory recording medium according to claim 3, wherein the degree of separation of each of the pieces of image data relative to the reference value is a degree of separation in a direction along the decision surface.

6. A case data generation support system comprising a computer configured to execute a process including:
   determining a reference value on a decision surface used for classifying a group of image data represented by a plurality of types of feature quantities into first and second classes in a feature quantity space, based on a feature quantity of a reference image data piece, the reference image data piece being closest to the decision surface in the feature quantity space and determined as belonging to the first class;
   plotting and displaying in a two-dimensional plane pieces of image data extracted from the group of image data, each of the plotted and displayed pieces of image data being distributed along each of two orthogonal axes of the two-dimensional plane in accordance with a degree of separation calculated for each of the pieces of image data relative to the reference value; and
   modifying, upon receiving a single piece of image data identified from among the plotted and displayed pieces of image data in the two-dimensional plane, the decision surface based on the identified single piece of image data;
   wherein the plotted and displayed pieces of image data in the two-dimensional plane include:
   pieces of image data to be determined as belonging to the first class plotted in a first region on an opposite side of the decision surface when viewed from a position of the reference image data piece; and
   pieces of image data to be determined as belonging to the second class plotted in a second region on the opposite side of the decision surface, the second region being visually distinct from the first region.

7. A case data generation support method executed by a computer, the method comprising:
   determining a reference value on a decision surface used for classifying a group of image data represented by a plurality of types of feature quantities into first and second classes in a feature quantity space, based on a feature quantity of a reference image data piece, the reference image data piece being closest to the decision surface in the feature quantity space and determined as belonging to the first class;
   plotting and displaying in a two-dimensional plane pieces of image data extracted from the group of image data, each of the plotted and displayed pieces of image data being distributed along each of two orthogonal axes of the two-dimensional plane in accordance with a degree of separation calculated for each of the pieces of image data relative to the reference value; and
   modifying, upon receiving a single piece of image data identified from among the plotted and displayed pieces of image data in the two-dimensional plane, the decision surface based on the identified single piece of image data;
   wherein the plotted and displayed pieces of image data in the two-dimensional plane include:
   pieces of image data to be determined as belonging to the first class plotted in a first region on an opposite side of the decision surface when viewed from a position of the reference image data piece; and
   pieces of image data to be determined as belonging to the second class plotted in a second region on the opposite side of the decision surface, the second region being visually distinct from the first region.

* * * * *